US009364282B2

(12) United States Patent
Just et al.

(10) Patent No.: US 9,364,282 B2
(45) Date of Patent: Jun. 14, 2016

(54) ABLATION ELECTRODE AND CATHETER ASSEMBLY FOR EPICARDIAL MAPPING AND ABLATION WITH DIRECTIONALLY FOCUSED RF ENERGY

(75) Inventors: Dale E. Just, Minneapolis, MN (US); James V. Kauphusman, Champlin, MN (US); Steven C. Christian, New Brighton, MN (US); Troy T. Tegg, Elk River, MN (US); Allan M. Fuentes, Mound, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 686 days.

(21) Appl. No.: 12/421,748

(22) Filed: Apr. 10, 2009

(65) Prior Publication Data

US 2009/0254078 A1    Oct. 8, 2009

Related U.S. Application Data

(63) Continuation-in-part of application No. PCT/US2007/080817, filed on Oct. 9, 2007, and a continuation-in-part of application No. PCT/US2007/080929, filed on Oct. 10, 2007.

(60) Provisional application No. 60/828,939, filed on Oct. 10, 2006.

(51) Int. Cl.
*A61M 3/02* (2006.01)
*A61B 18/14* (2006.01)
(Continued)

(52) U.S. Cl.
CPC ............. *A61B 18/1492* (2013.01); *A61B 5/042* (2013.01); *A61B 5/0422* (2013.01);
(Continued)

(58) Field of Classification Search
CPC ....... A61B 5/422; A61B 18/18; A61B 5/1492
USPC ............................................... 606/41–42, 45
See application file for complete search history.

(56) References Cited

U.S. PATENT DOCUMENTS 4,890,623 A   1/1990   Cook et al.
5,080,660 A   1/1992   Buelna
(Continued)

FOREIGN PATENT DOCUMENTS

WO    2005032362 A2    4/2005

OTHER PUBLICATIONS

Stephen C. Hammill, M.D., Epicardial Ablation: Reducing the Risks, J. Cardiovasc Electrophysiol, vol. 17, pp. 550-552, May 2006.
(Continued)

*Primary Examiner* — Edelmira Bosques
(74) *Attorney, Agent, or Firm* — Dykema Gossett PLLC

(57) ABSTRACT

The present invention provides various embodiments of electrodes and/or electrode tips for use in connection with ablation catheters and ablation catheter systems. In an embodiment, an electrode tip for an ablation catheter is provided, comprising an electrode carrier, a first electrode, and second electrode, each adapted to direct energy is various directions and configured to be selectively activated. In another embodiment, an electrode is provided that comprises an electrode body having an insulated portion to protect adjacent tissue from ablation while further adapted to direct energy in a downward direction towards the target tissue. Other embodiments of electrodes and/or electrode tips providing ablative elements that are directed laterally are also disclosed. Moreover, embodiments of several types of electrodes and/or electrode tips, which may include positioning, orientation, irrigating, cooling, and deflecting features, whether provided individually or in various combinations, are also disclosed.

25 Claims, 38 Drawing Sheets

(51) Int. Cl.
*A61B 5/042* (2006.01)
*A61B 5/00* (2006.01)
*A61M 25/01* (2006.01)
*A61B 18/18* (2006.01)
*A61B 18/00* (2006.01)
*A61N 7/02* (2006.01)

(52) U.S. Cl.
CPC .......... *A61B5/6852* (2013.01); *A61M 25/0147* (2013.01); *A61B 18/18* (2013.01); *A61B 18/1815* (2013.01); *A61B 2018/0016* (2013.01); *A61B 2018/00023* (2013.01); *A61B 2018/00029* (2013.01); *A61B 2018/00214* (2013.01); *A61B 2018/00244* (2013.01); *A61B 2018/00285* (2013.01); *A61B 2018/00351* (2013.01); *A61B 2018/00577* (2013.01); *A61B 2018/00839* (2013.01); *A61B 2018/00898* (2013.01); *A61B 2018/1467* (2013.01); *A61B 2018/1497* (2013.01); *A61B 2560/066* (2013.01); *A61B 2562/222* (2013.01); *A61N 7/02* (2013.01); *Y10T 29/4913* (2015.01)

(56) References Cited

U.S. PATENT DOCUMENTS

| | | | |
|---|---|---|---|
| 5,318,525 A | | 6/1994 | West et al. |
| 5,348,554 A | | 9/1994 | Imran et al. |
| 5,403,311 A | * | 4/1995 | Abele et al. ............ 606/49 |
| 5,476,495 A | | 12/1995 | Kordis et al. |
| 5,571,085 A | | 11/1996 | Accisano |
| 5,681,282 A | * | 10/1997 | Eggers et al. ............ 604/114 |
| 5,683,366 A | * | 11/1997 | Eggers et al. ............ 604/114 |
| 5,728,094 A | * | 3/1998 | Edwards ............ 606/41 |
| 5,755,766 A | | 5/1998 | Chastain et al. |
| 5,766,153 A | * | 6/1998 | Eggers et al. ............ 604/114 |
| 5,785,705 A | | 7/1998 | Baker |
| 5,797,903 A | * | 8/1998 | Swanson ............ A61L 29/085 600/374 |
| 5,843,152 A | * | 12/1998 | Tu et al. ............ 607/122 |
| 5,885,238 A | | 3/1999 | Stevens et al. |
| 5,954,665 A | | 9/1999 | Ben-Haim |
| 6,015,407 A | * | 1/2000 | Rieb et al. ............ 606/41 |
| 6,117,088 A | | 9/2000 | Kreizman et al. |
| 6,168,593 B1 | | 1/2001 | Sharkey et al. |
| 6,210,406 B1 | | 4/2001 | Webster |
| 6,226,554 B1 | | 5/2001 | Tu et al. |
| 6,277,107 B1 | | 8/2001 | Lurie et al. |
| 6,394,956 B1 | | 5/2002 | Chandrasekaran et al. |
| 6,494,880 B1 | | 12/2002 | Swanson et al. |
| 6,517,477 B1 | | 2/2003 | Wendlandt |
| 6,544,215 B1 | | 4/2003 | Bencini et al. |
| 6,554,794 B1 | | 4/2003 | Mueller |
| 6,602,242 B1 | * | 8/2003 | Fung et al. ............ 604/528 |
| 6,726,677 B1 | * | 4/2004 | Flaherty et al. ............ 604/528 |
| 6,743,239 B1 | | 6/2004 | Kuehn et al. |
| 6,945,956 B2 | | 9/2005 | Waldhauser et al. |
| 7,717,899 B2 | | 5/2010 | Bowe et al. |
| 2001/0007070 A1 | | 7/2001 | Stewart |
| 2002/0029030 A1 | | 3/2002 | Lurie et al. |
| 2002/0111618 A1 | | 8/2002 | Stewart et al. |
| 2002/0128639 A1 | * | 9/2002 | Pless et al. ............ 606/27 |
| 2002/0165537 A1 | | 11/2002 | Kelley et al. |
| 2003/0050637 A1 | | 3/2003 | Maguire et al. |
| 2003/0114832 A1 | | 6/2003 | Kohler et al. |
| 2004/0030331 A1 | | 2/2004 | Thomas et al. |
| 2004/0143256 A1 | * | 7/2004 | Bednarek ............ 606/41 |
| 2005/0065508 A1 | | 3/2005 | Johnson et al. |
| 2005/0159799 A1 | * | 7/2005 | Daglow et al. ............ 607/116 |
| 2005/0234436 A1 | | 10/2005 | Baxter et al. |
| 2005/0272975 A1 | | 12/2005 | McWeeney et al. |
| 2006/0100618 A1 | | 5/2006 | Chan et al. |
| 2007/0179486 A1 | | 8/2007 | Welch et al. |
| 2010/0094279 A1 | | 4/2010 | Kauphusman |
| 2012/0029334 A1 | | 2/2012 | Tegg |

OTHER PUBLICATIONS

Robert A. Schweikert, M.D. et al., Percutaneous Pericardial Instrumentation for Endo-Epicardial Mapping of Previously Failed Ablations, Circulation 2003; 108; 1329-1335; originally published online Sep. 2, 2003.

"Supplementary European Search Report", EP 07844081 Jun. 15, 2011.

"Supplementary European Search Report", EP 07 84 4086 Jun. 6, 2011.

* cited by examiner

ABLATION ELECTRODE AND CATHETER ASSEMBLY FOR EPICARDIAL MAPPING AND ABLATION WITH DIRECTIONALLY FOCUSED RF ENERGY

CROSS-REFERENCE TO RELATED APPLICATIONS

This application is a continuation-in-part of International Application No. PCT/US2007/080929 filed Oct. 10, 2007, and International Application No. PCT/US2007/080817 filed Oct. 9, 2007, the entire disclosures of which is are both incorporated herein by reference, both of which claim the benefit of priority of U.S. Provisional Application 60/828,939 filed Oct. 10, 2006.

BACKGROUND OF THE INVENTION

A. Field of the Invention

The present invention generally relates to electrodes/electrode tips and ablation systems. Aspects of the invention involve catheter-based ablation systems useful for ablating biological tissue, including the treatment of heart conditions. More particularly, the present invention includes electrodes/electrode tips and insulated catheter ablation systems for use in epicardial procedures, such as those used for the treatment of atrial fibrillation or ventricular tachycardia.

B. Background Art

Catheters have been in use for medical procedures for a number of years. For example, one procedure, often referred to as "catheter ablation," utilizes a catheter to convey energy to a selected location within the human body. Another procedure oftentimes referred to as "mapping" utilizes a catheter with sensing electrodes to monitor various forms of electrical activity in the human body.

Moreover, catheters are increasingly used for medical procedures involving the human heart, including the treatment of certain types of ventricular arrhythmia and atrial arrhythmia. Such procedures commonly involve the ablation of tissue in the heart and are performed many times with an ablation catheter. Ablation catheters are commonly inserted in an artery or vein in the leg, neck, or arm of the patient and threaded, sometimes with the aid of a guidewire or introducer, through the vessels until the distal tip of the ablation catheter reaches a desired location for the ablation procedure. The ablation catheters commonly used to perform such procedures often electrically isolate or render the tissue non-contractile at particular points by physical contact of the tissue with an electrode of the ablation catheter and the application of energy.

In some conventional ablation procedures, the ablation catheter includes a single distal electrode secured to the tip of the ablation catheter to produce small lesions wherever the tip contacts the tissue during energy application. To produce a linear lesion, the tip may be dragged slowly along the tissue during energy application. Increasingly, however, cardiac ablation procedures utilize multiple electrodes affixed to the catheter body to form multiple lesions.

Traditional ablation electrodes provide an electrically conductive surface on the entire surface of the electrode, thereby potentially ablating surfaces of surrounding tissue, in particular, the pericardial sac when attempting to ablate the epicardial surface of the heart. Another challenge in obtaining an adequate ablation treatment using conventional ablation catheters is the constant movement of the heart, particularly when there is an erratic or exhibits an irregular heart beat. Another challenge in obtaining an adequate ablation treatment is associated with the inability of conventional catheters to obtain and retain sufficient contact with target tissue along or across various tissue surfaces.

BRIEF SUMMARY OF THE INVENTION

It is desirable to be able to provide a means for more selectively ablating tissue at a target site using minimally invasive approaches. It is further desirable to be able to provide a means for more selectively ablating tissue unidirectionally at a target site using minimally invasive approaches, as well as to better protect non-targeted tissue from ablation. Moreover, it is desirable to provide improved surface-to-surface contact between the ablative element and the targeted tissue.

The present invention provides various embodiments of electrodes for use in connection with an ablation catheter and ablation catheter systems. In an embodiment, an electrode tip is provided that comprises an electrode carrier; a first electrode provided at a distal portion of the electrode carrier, the first electrode adapted to direct energy in a forward longitudinal direction; and a second (e.g., side-firing) electrode provided at a side portion of the electrode carrier, the second electrode adapted to direct energy in a lateral direction. In an embodiment the first and second electrodes can be selectively activated. Other embodiments of electrode tips that provide ablative elements that are directed laterally are also disclosed.

In another embodiment, an electrode is provided that comprises an electrode body defining an outer surface, a top portion and a bottom portion. The top portion of the electrode body includes an insulated portion to protect adjacent tissue from ablation. The bottom portion is adapted to direct energy in a downward direction towards the target tissue. Moreover, embodiments of several types of electrodes and/or electrode tips, which may include positioning, orientation, irrigating, cooling, and deflecting features, whether provided individually or in various combinations, are also disclosed.

The foregoing and other aspects, features, details, utilities, and advantages of the present invention will be apparent from reading the following description and claims, and from reviewing the accompanying drawings.

DETAILED DESCRIPTION OF THE INVENTION

Figure 1:
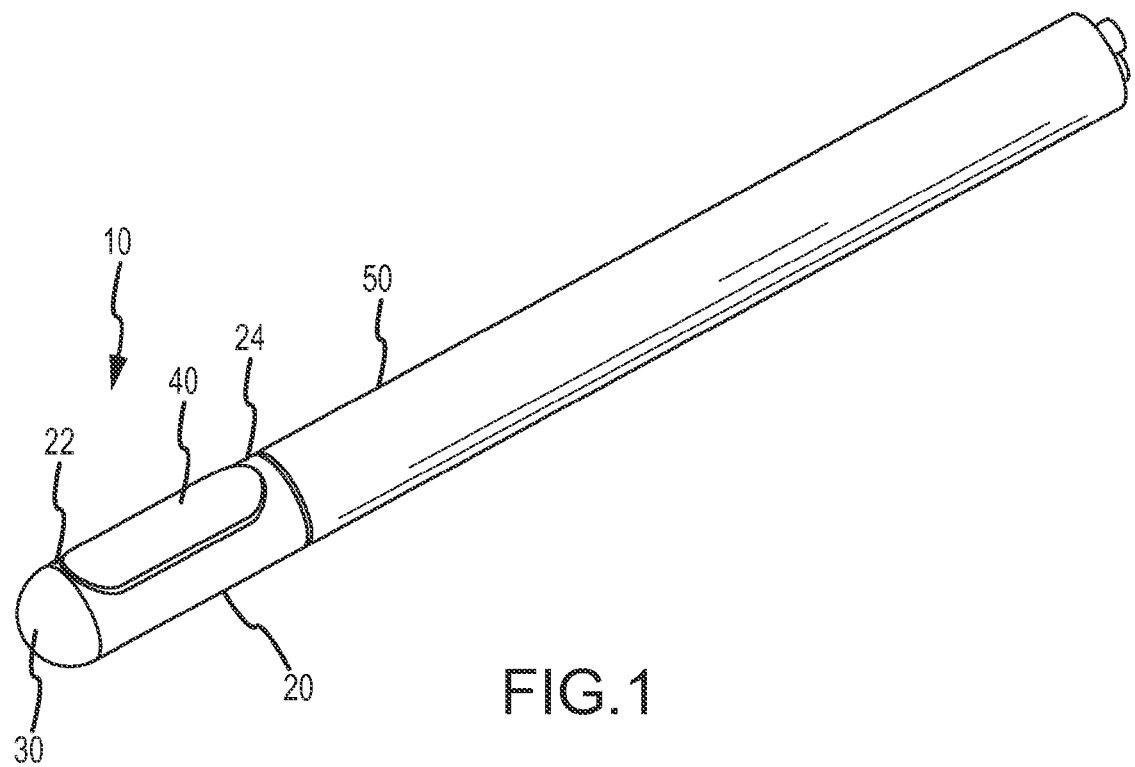
FIG. 1 is a perspective view of an electrode tip in accordance with an embodiment of the invention.

In general, the present invention relates to electrodes/electrode tips and ablation systems for use in performing epicardial ablation procedures. Moreover, the present invention relates to electrodes and insulated catheter ablation systems for use in epicardial procedures, such as those used for the treatment of atrial fibrillation. Moreover, the electrodes and catheter systems may be interchanged or switched with one another depending on the intended operation of the selected medical tool. For purposes of this description, similar aspects among the various embodiments described herein may be referred to by the same reference number. As will be appreciated, however, the structure of the various features may differ with respect to alternate embodiments.

During the performance of epicardial ablation procedures, it is necessary to obtain access within the pericardial sac surrounding the heart. In order to access the pericardial sac and reach the epicardial surface, it can be desirable to use shorter devices compared to those traditionally used in cardiac procedures. Accordingly a relatively shorter steerable access device, or introducer, may be used rather than the traditional access devices in order to enable effective access to the epicardial surface of the heart through the pericardial sac. In addition, the shorter steerable access device may be comprised of a flexible elongated member that can readily reflect the curvature or profile of organs, i.e. the heart, therein defining a gradual curvature of the sheath for positioning the access device within the pericardial sac and ultimately in relation to the epicardial surface of the heart for performance of various procedures. Once the shorter steerable access device in put into position between the pericardial sac and epicardial surface, various modified tools and/or devices are inserted into the inner lumen of the access sheath for performing various functions throughout the procedure The present invention provides various embodiments of electrode tips and/or electrodes and catheter assemblies that, for example, may be used in connection with an access sheath (e.g. a short steerable access sheath) for accessing the epicardial surface of the heart. In particular, the present invention provides various electrodes tips and related assemblies that can provide an insulating member to protect non-targeted areas (e.g., the pericardial sac) from the ablative surface of the electrode, as well as deliver consistent and unimpeded ablative energy, such as, for example, radiofrequency energy, unidirectionally (e.g., in a first direction, and not a second direction). Moreover, the present invention further provides tools or devices to aid in determining the orientation of the catheter shaft and electrode such that the physician will know that ablative surface of the electrode is properly directed towards the target tissue (e.g. epicardial surface) while the insulated member or portion of the electrode may be positioned adjacent to the non-target tissue (e.g., the pericardial sac).

Figure 2:
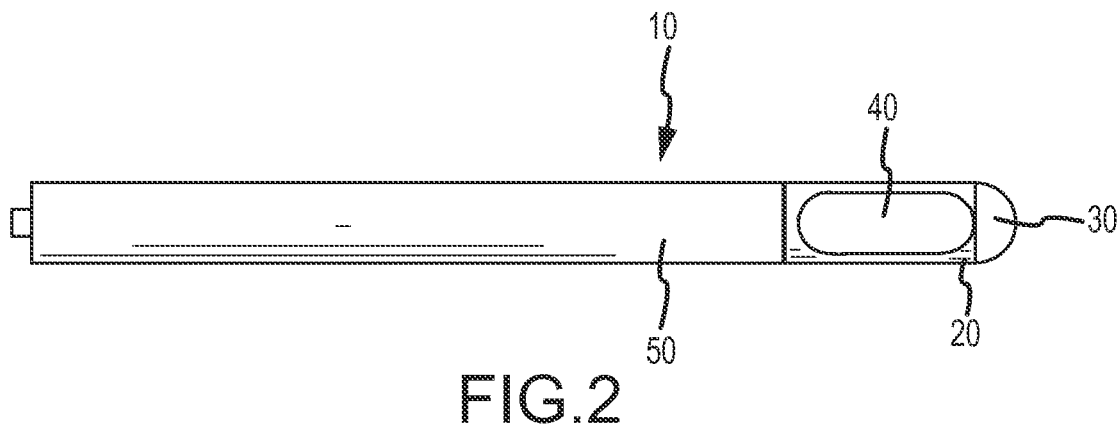
FIG. 2 is a top view of the electrode tip of FIG. 1.
Figure 3:
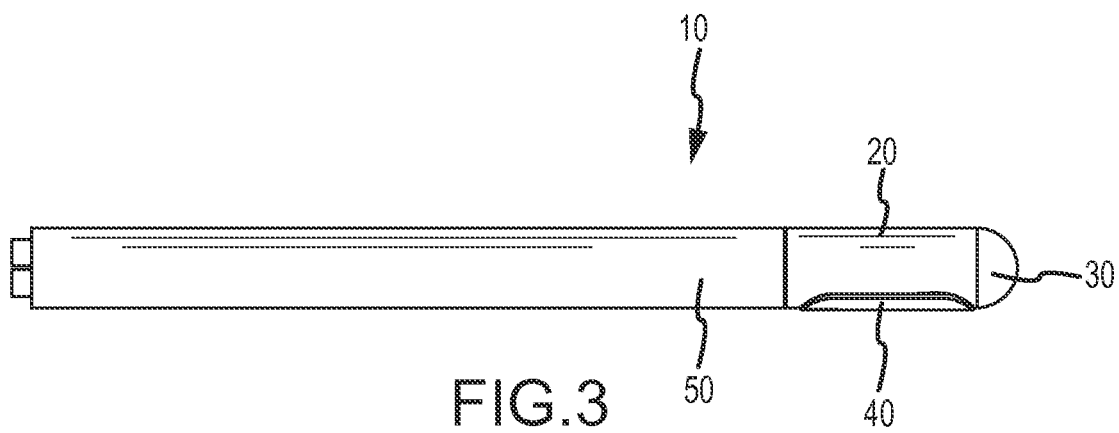
FIG. 3 is a side view of the electrode tip of FIG. 1.

FIG. 1 illustrates an electrode tip 10 according to an embodiment of the invention. FIGS. 2 and 3 illustrate a top and side view of an electrode tip 10 of the type generally shown in FIG. 1. The illustrated electrode tip 10 includes an electrode carrier 20, including a distal portion 22 and a proximal portion 24; a first electrode 30; and a second electrode 40. As generally illustrated, electrode tip 10 may be adapted for connection to a portion of a catheter 50.

In an embodiment, the first electrode 30 is provided at the distal portion 22 of the electrode carrier 20. The first electrode 30 is adapted to direct energy in at least a forward longitudinal direction. For some embodiments, the exposed or potentially active portion of the first electrode 30 may be reduced, for example by providing an electrode with a different shape and/or covering a portion of the electrode with an insulated or isolative material that prevents transmission of energy into tissue not targeted for ablation. Consequently, depending upon the configuration of the first electrode, and the degree of non-insulated exposure, some portion of the energy conveyed by the first electrode 30 may also be directed in other than a forward longitudinal direction.

The second electrode 40 is provided at a side portion of the electrode carrier 20. The second electrode is adapted to direct energy in a first side or lateral direction relative to the electrode carrier 20, and not in a second side or lateral direction relative to the electrode carrier 20. As generally illustrated in FIGS. 1 and 2, the second electrode 40 may be generally oval and may extend outwardly, to some degree (for example as shown in FIG. 3) from the adjacent surface of the electrode carrier 20. However, the invention is not limited to such a configuration, and other configurations and positioning of the electrode carrier 20, including, without limitation, those illustrated in other embodiments disclosed herein are contemplated by the invention.

The first and/or second electrodes 30,40 may be configured to energize and ablate tissue, may additionally be a sensing electrode (for example, to provide a mapping function), and/or may include other functionality. Moreover, the first and/or second electrodes 30,40 may include one or more wires or lines that are provided or strung through a catheter to a proximal region of the catheter.

Figure 4:
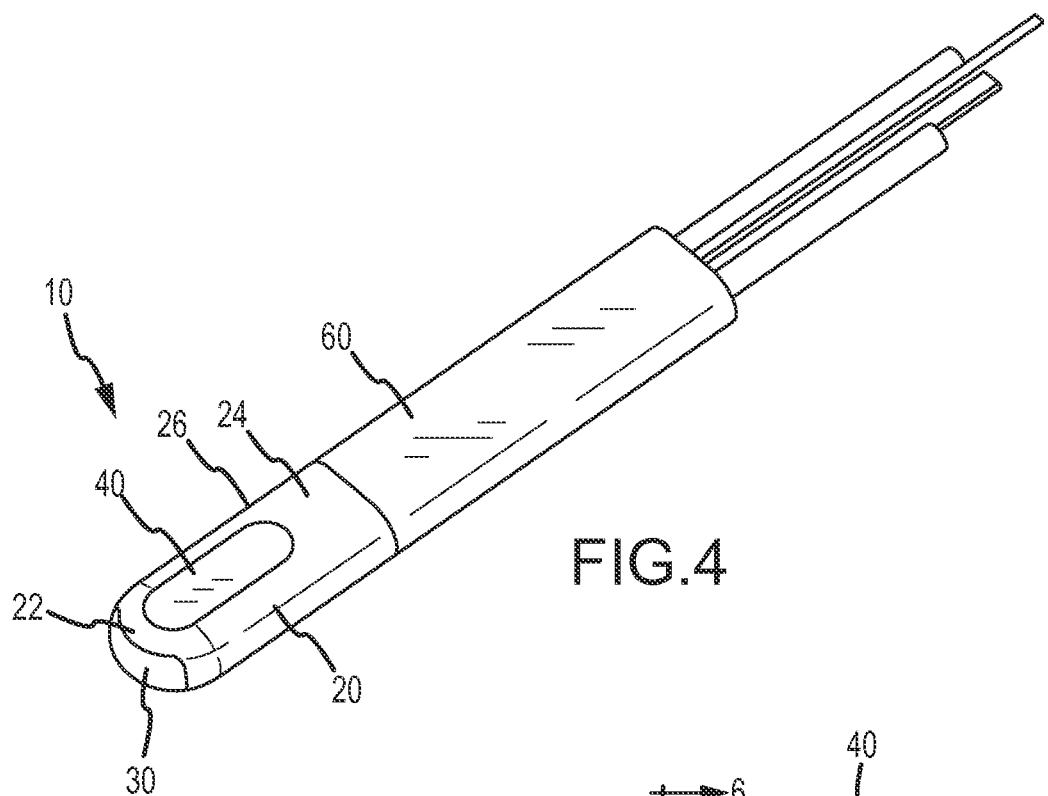
FIG. 4 is a perspective view of an electrode tip in accordance with another embodiment of the present invention.
Figure 5:
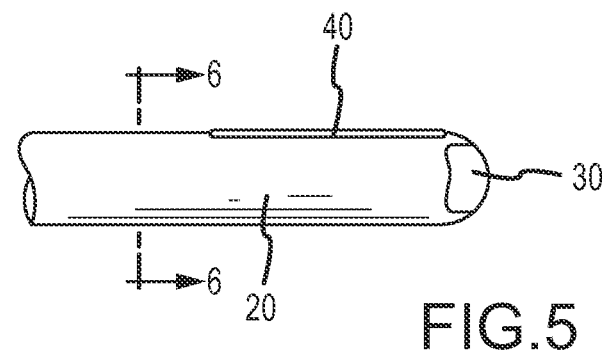
FIG. 5 is a side view of the electrode tip shown in FIG. 4.
Figure 6:
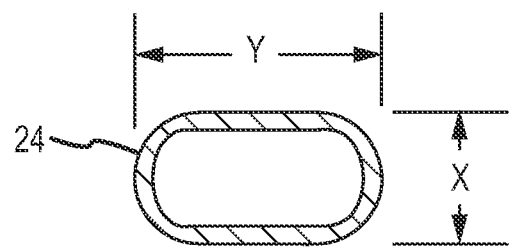
FIG. 6 is a cross-sectional view of the electrode carrier included with the tip viewed along lines 6-6 in FIG. 5.

FIGS. 4-6 generally illustrate another embodiment of an electrode tip that also includes a first electrode 30 and a second electrode 40. In this embodiment, the electrode tip comprises a non-circular cross-section, which may take the form of an oval cross-section, such as shown in FIGS. 5 and 6. Further, for some embodiments, it may be desirable for the electrode tip 10 to include an orientation feature that can help indicate to a user that the tip 10 is appropriately directed toward a the targeted tissue. In addition to including a means for measuring impedance (including that discussed further in connection with other embodiments), the inventive concept may, instead of or in addition to, provide a portion of the electrode tip, particularly a portion near or adjacent side electrode 40, with a geometry that, at least to some degree, is more stable and resistant to a "rolling" movement than an electrode carrier with a circular or curved outer surface and/or provides some mechanical or physical feedback (e.g., resistance to twisting or rotation) with respect to the positioning of the operative portion of the electrode tip 10 relative to a surface. For example, in the embodiment illustrated in FIGS. 4-6, the electrode carrier 20 includes a surface 26 with "flat" (i.e., flat or substantially flat) portions adjacent the second electrode 40—for example at or about the distal and proximal portions 22, 24 illustrated in FIG. 4. Moreover, as generally illustrated in the cross section of the electrode carrier 20, the carrier may generally have a first dimension X and a second dimension Y. For some embodiments, second dimension Y will be at least 1.5 times dimension X. For other embodiment, dimension Y will be two or more times dimension X.

As generally illustrated in FIG. 4, the electrode tip may be connected to a catheter extension 60. The catheter extension 60 may be configured to provide a connective transition between electrode tip 10 and a distal portion of catheter 50. In alternative embodiments, electrode tip may include an extension portion that is formed integrally with a portion the electrode tip.

In an embodiment, the first and second electrodes can be selectively activated. For example, depending upon the circumstances, such as the area of target tissue intended to be subjected to ablation, the first electrode 30 may be "off" or inactive, while the second electrode 40 is "on" or active. For other circumstances, the first electrode may be "on" for distal end contact, while the second electrode 40 is "off." Such selective control may be provided via a remote (relative to the electrode tip) switch or control that may be associated with the energy or power source associated with each electrode. Moreover, there may be some circumstances in which it is desirable for both electrodes to be simultaneously active or inactive.

The energy associated with the first and/or second electrodes 30, 40 may be radio frequency (RF) energy provided via a catheter from one or more RF energy source or sources. However, the invention is not limited to such a source of energy, and other energy forms that permit the desired directional control associated with the electrodes may also be used. For example, without limitation, focused ultrasound, shielded microwave, and other energy sources, particularly those with a directional aspect, may also be employed with embodiments of the invention.

Figure 7:
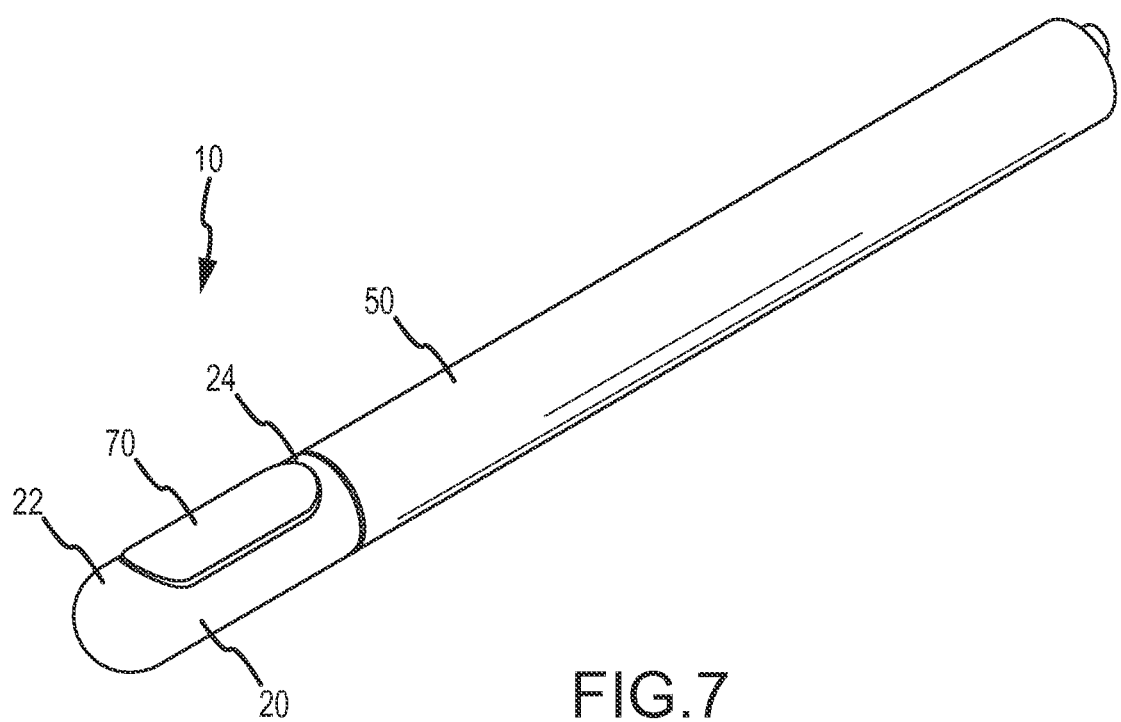
FIG. 7 is a perspective view of an electrode tip in accordance with an embodiment of the invention.

FIG. 7 illustrates an electrode tip 10 according to another embodiment of the invention. The illustrated electrode tip 10 includes an electrode carrier 20, including a distal portion 22 and a proximal portion 24; and a side electrode 70, which functions similarly to the aforementioned second electrode 40. As generally illustrated, electrode tip 10 may be adapted for connection to a portion of a catheter 50 or various forms of catheter extensions. Optionally, and to the extent the overall width of the electrode tip can be configured for an intended application, a second similar side electrode (not shown) may be provided and positioned on the electrode tip, for example, about 180° from the illustrated side electrode 70. Further, as discussed in connection with prior multiple-electrode embodiments, the electrodes may be selectively activated.

Figure 8:
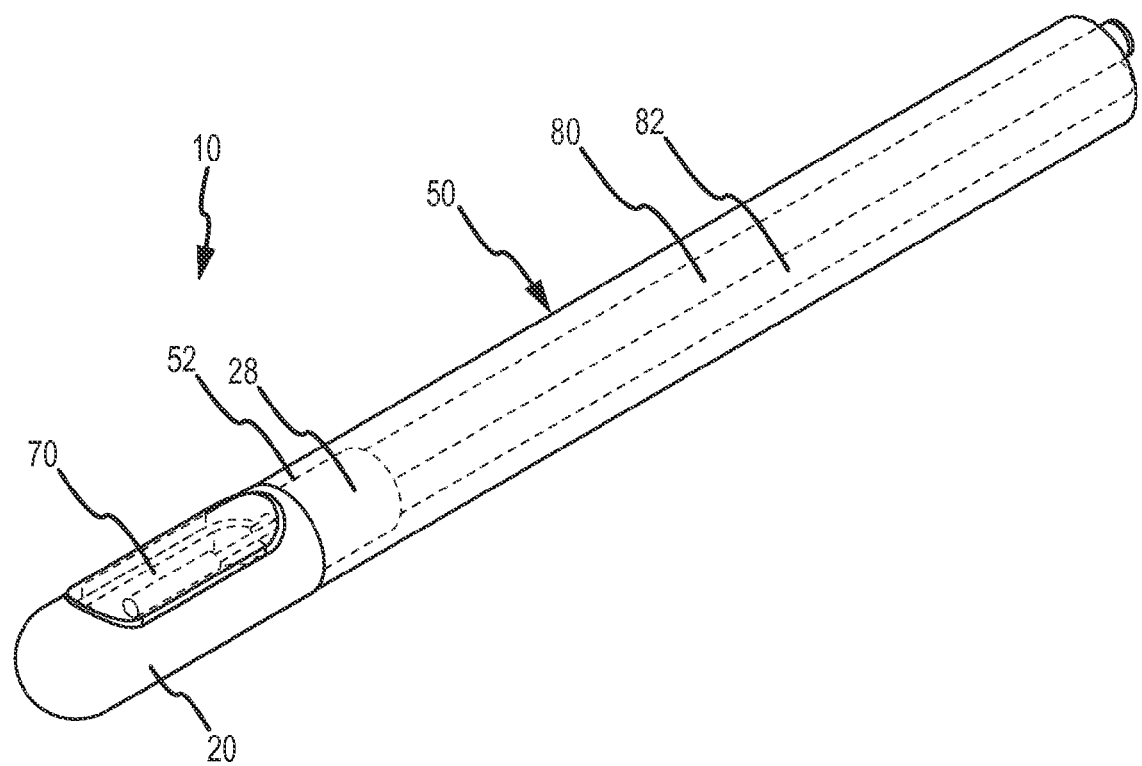
FIG. 8 is a partial cut-away view of the electrode tip of FIG. 7.
Figure 9:
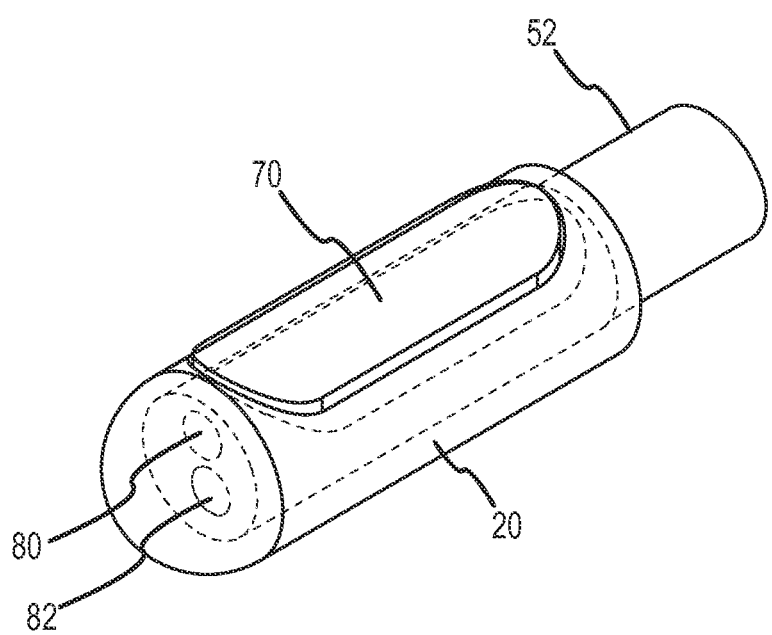
FIG. 9 is a perspective view of an electrode tip in accordance with an embodiment of the invention, showing portions of the tip in phantom.
Figure 10:
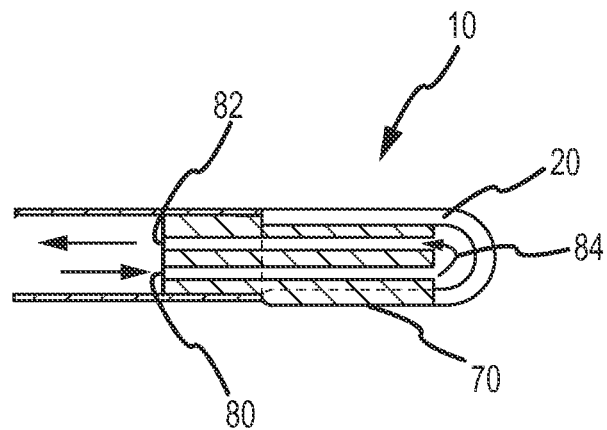
FIG. 10 is cross-sectional representation of an electrode tip in accordance with an embodiment of the invention.
Figure 11:
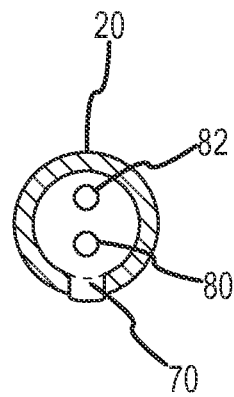
FIG. 11 is a cross-sectional view of the electrode tip of FIG. 10.
Figure 12:
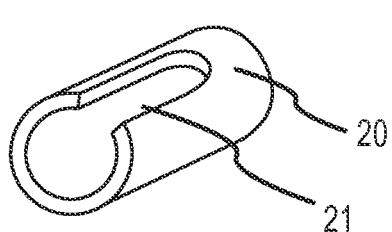
FIG. 12 is a perspective view of an embodiment of an electrode carrier in accordance with an embodiment of the invention.
Figure 13:
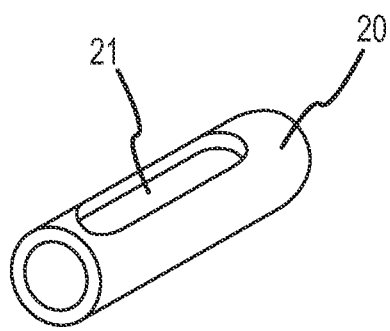
FIG. 13 is a perspective view of another embodiment of an electrode carrier in accordance with an embodiment of the invention.
Figure 14:
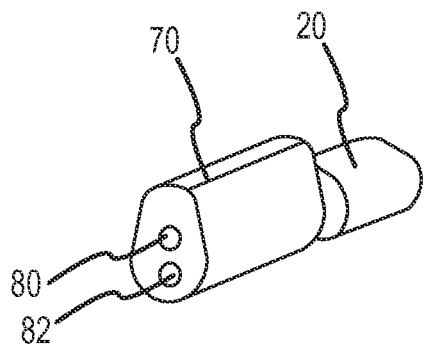
FIG. 14 is a general representation and partial view illustration of a manner of assembling an electrode and an electrode carrier.
Figure 15:
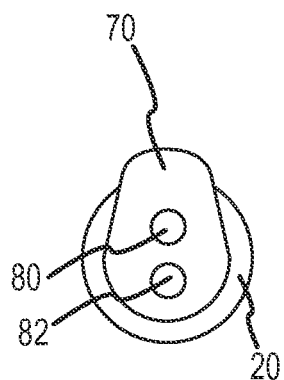
FIG. 15 is an end view of an assembled electrode and an electrode carrier.

As better illustrated in the cut-away view of the electrode tip 10 shown in FIG. 8, a portion 28 of the electrode carrier 20 may be adapted to be connected to a portion of catheter 50. For example, without limitation, a portion 52 of catheter 50 may surround and be firmly secured or connected to portion 28 of the electrode carrier 20.

The invention also contemplates the optional inclusion of a means for providing irrigation and/or cooling to at least a portion of the electrode tip 10. For example, as generally shown in FIGS. 8-11, electrode tip 10 may include one or more lines, passages and/or conduits 80, 82 for transmitting a fluid to and/or from the electrode tip 10. As shown, in an embodiment, the line, passage, and/or conduit that supplies a fluid (such as a cooling fluid, e.g., saline) may be provided about or in close proximity to the portion of the electrode tip 10 that performs the ablation, and, for some embodiments, an open tip portion 84 may be provided at or near the distal end of the electrode tip 10.

The invention also contemplates the optional inclusion of a means for providing irrigation and/or cooling to at least a portion of the electrode tip 10. For example, as generally shown in FIGS. 8-11, electrode tip 10 may include one or more lines, passages and/or conduits 80, 82 for transmitting a fluid to and/or from the electrode tip 10. As shown, in an embodiment, the line, passage, and/or conduit that supplies a fluid (such as a cooling fluid, e.g., saline) may be provided about or in close proximity to the portion of the electrode tip 10 that performs the ablation, and, for some embodiments, an open tip portion 84 may be provided at or near the distal end of the electrode tip 10. Lines, passages and/or conduits 80, 82 as described hereinabove can comprise means for providing cooling to external portions adjacent the first or second electrode 30 or 40.

In an embodiment, the electrode tip (e.g., electrode carrier) may include an external porous membrane, and/or one or more external openings or orifices, to provide localized cooling to portions of the electrode tip in proximity to non-targeted surrounding areas or tissue. For example, a portion of the electrode carrier may be comprised of a material that permits controlled weeping. In an embodiment, a porous membrane may be provided that is comprised, at least in part, of a polymer (e.g., a sintered expanded PTFE) that includes an open lattice construction. In yet another embodiment, the structure supporting the ablative element of the electrode tip may be comprised of a porous material to permit localized irrigation and/or cooling for nearby non-target tissue. Electrode carrier 20 can comprise an external porous membrane and/or can include one or more external openings or orifices that can comprise means for providing cooling to external portions adjacent the first or second electrode 30 or 40.

Figure 16:
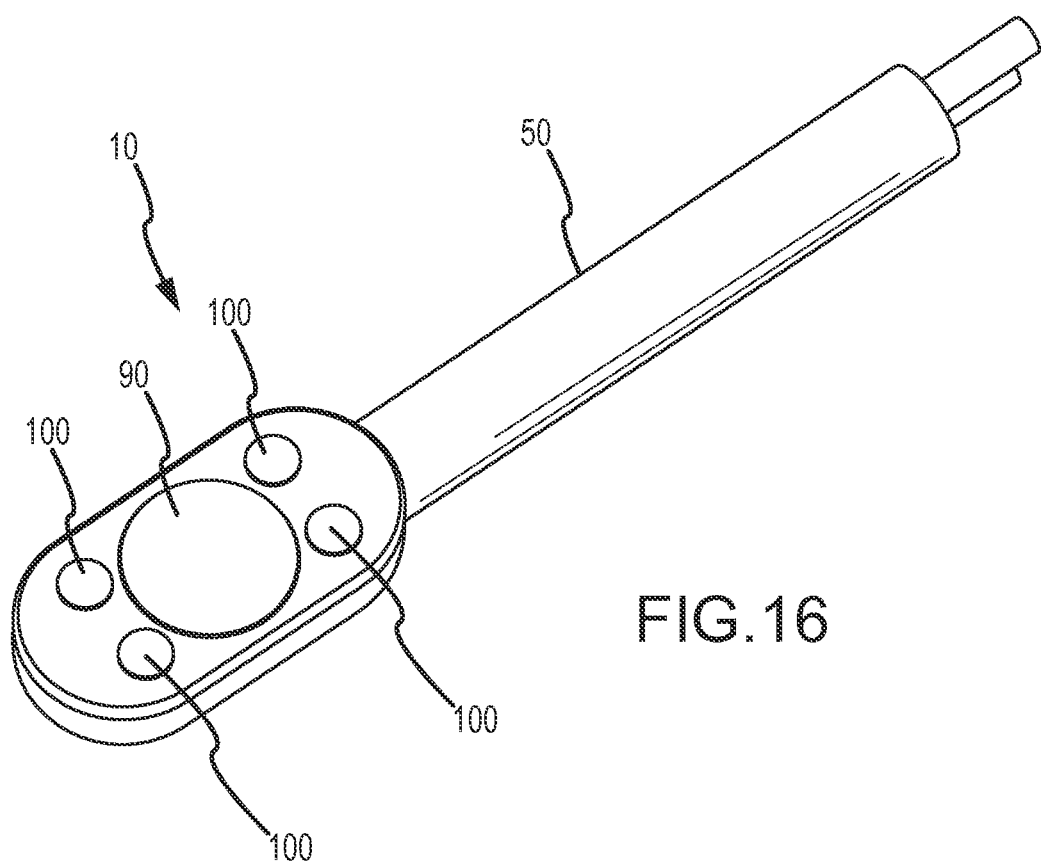
FIG. 16 is a perspective view of an electrode tip in accordance with an embodiment of the invention.

Another embodiment of an electrode tip 10 is generally illustrated in FIG. 16. As generally shown, the electrode tip 10 may take on a "paddle"-like shape, and, if desired, may include more than one electrode. For example, in the illustrated embodiment, the electrode tip 10, includes a round, central electrode 90, and additionally includes a plurality of relatively smaller round EGM button electrodes 100.

Figure 17:
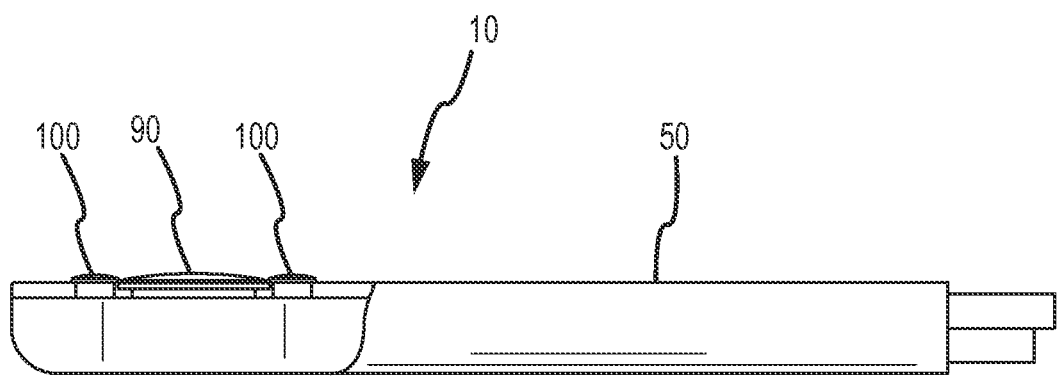
FIG. 17 is a partial exposed view of an electrode tip as shown in FIG. 16.

FIGS. 17-20 illustrate additional views of an electrode tip 10 of the type shown in FIG. 16, as well as various sub-combinations thereof. Turning to FIG. 17, a side view of an electrode tip 10 is shown with a portion (see, e.g., element 102 in FIG. 20) of the electrode carrier 20 about the electrodes 90, 100 removed. Depending upon the desired method of manufacturing, the removed portion 102 may be formed integrally with the remainder of the electrode carrier 20.

Figure 18:
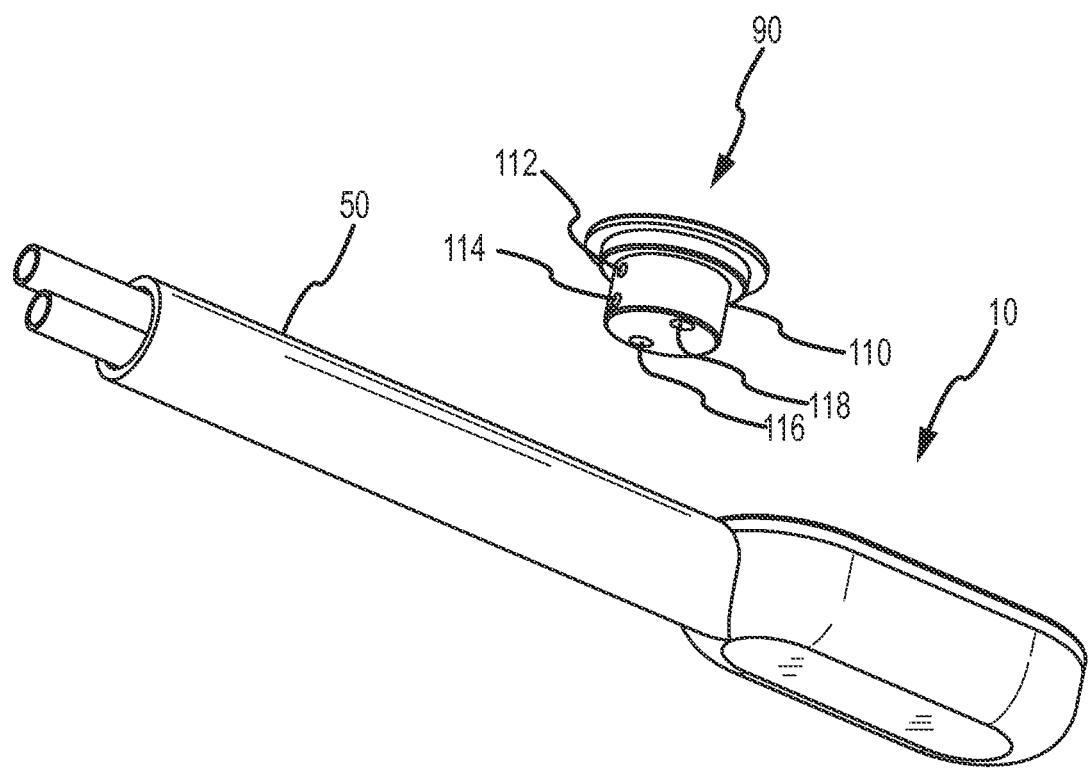
FIG. 18 is a partial cut-away view of an electrode tip as shown in FIG. 16, viewed from the bottom and shown with the central electrode removed.
Figure 19:
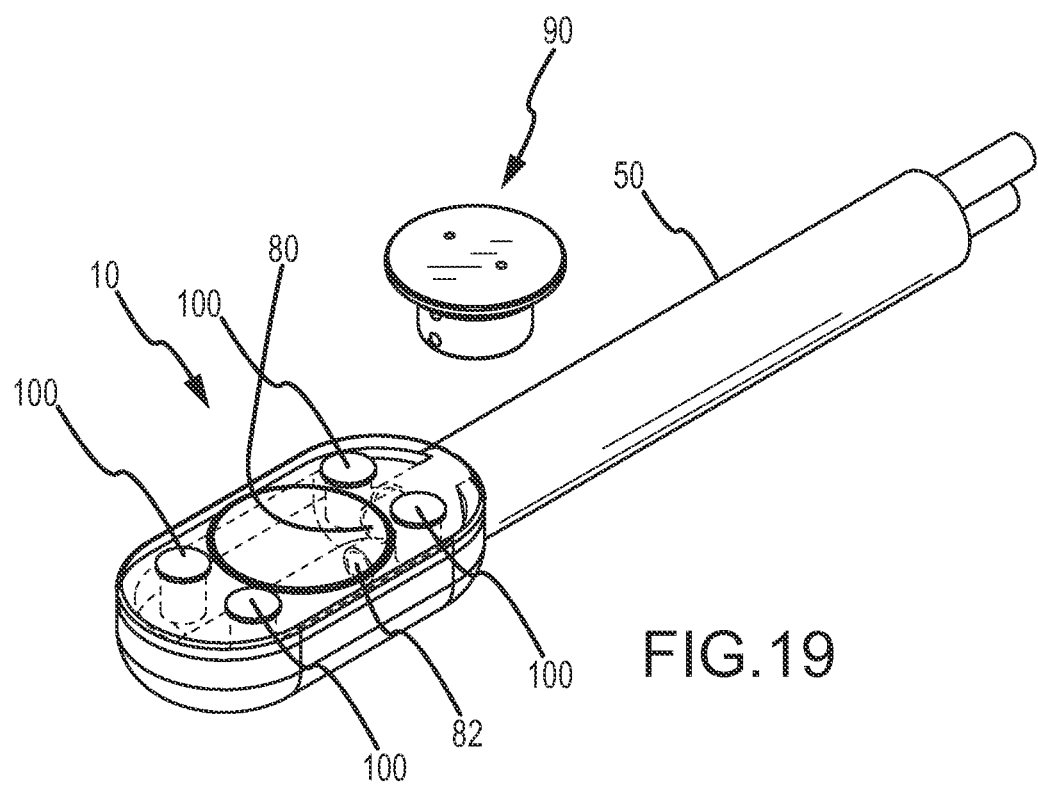
FIG. 19 is another partial cut-away view of an electrode tip as shown in FIG. 16, viewed from above and shown with a portion of the electrode carrier and the central electrode removed.
Figure 20:
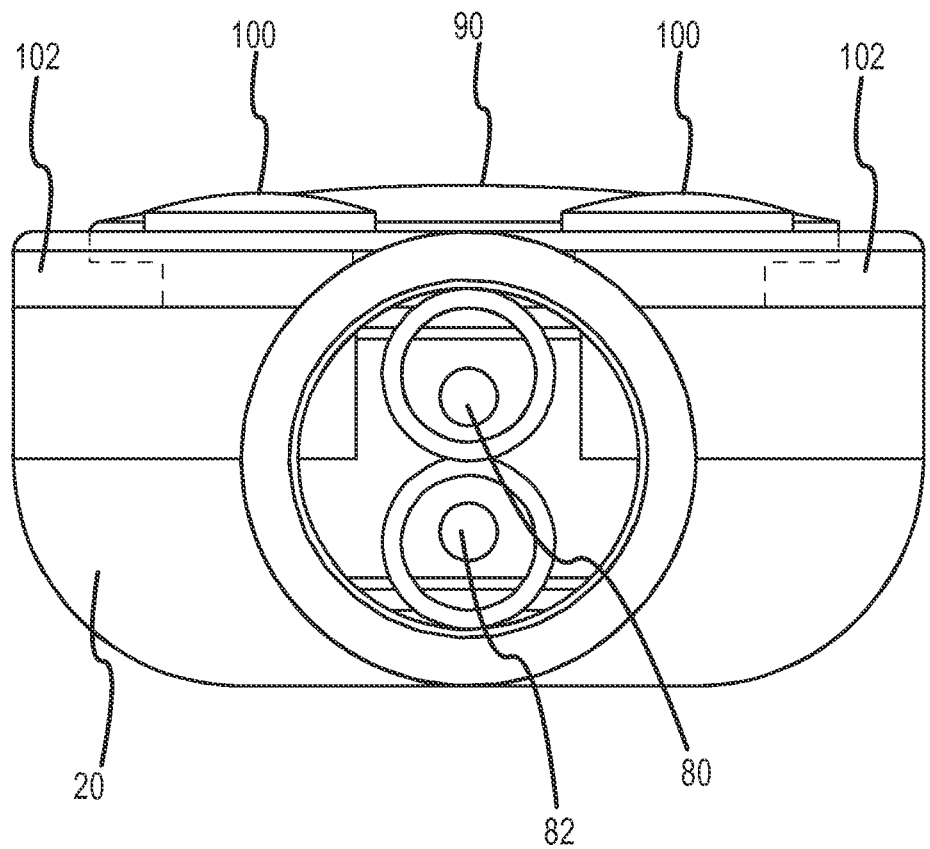
FIG. 20 is another partial cut-away view of an electrode tip as shown in FIG. 16, viewed from the direction of an associated catheter.

FIGS. 18 and 19 illustrate views of the electrode tip 10 shown with electrode 90 removed. As generally illustrated in this figure, the electrode 90 may additionally include an extension 110 and may further include one or more horizontal passages (e.g., 112, 114), which may be connected to cooling fluid passages (e.g., 80, 82) and/or one or more vertical passages (e.g., 116, 118). Such passages may, among other things, be configured to provide energy and/or cooling fluid to the electrode and/or in the vicinity of the intended ablation area. While various specifics, including specific configurations of components, have been disclosed, the invention is not so limited, and a wide number of alternative configurations may be readily contemplated by those of skill in the art and are encompassed by the present invention as embodied in the claims.

Figure 21:
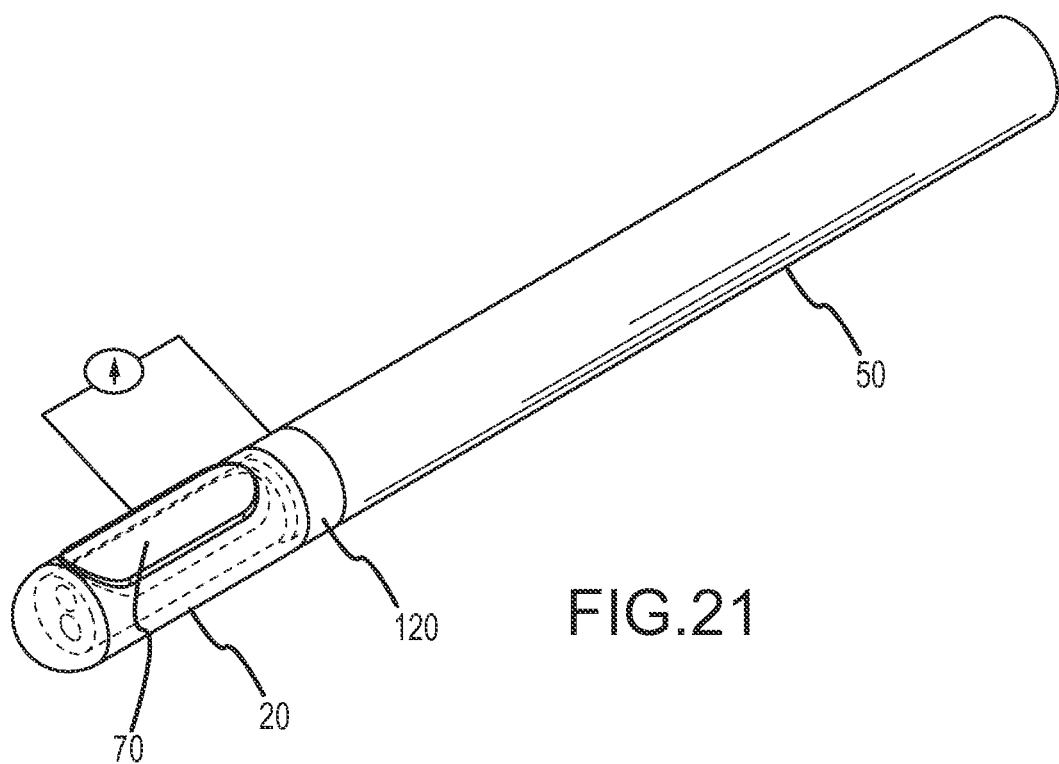
FIG. 21 is partial cut-away view of an electrode tip according to an embodiment of the invention.
Figure 22:
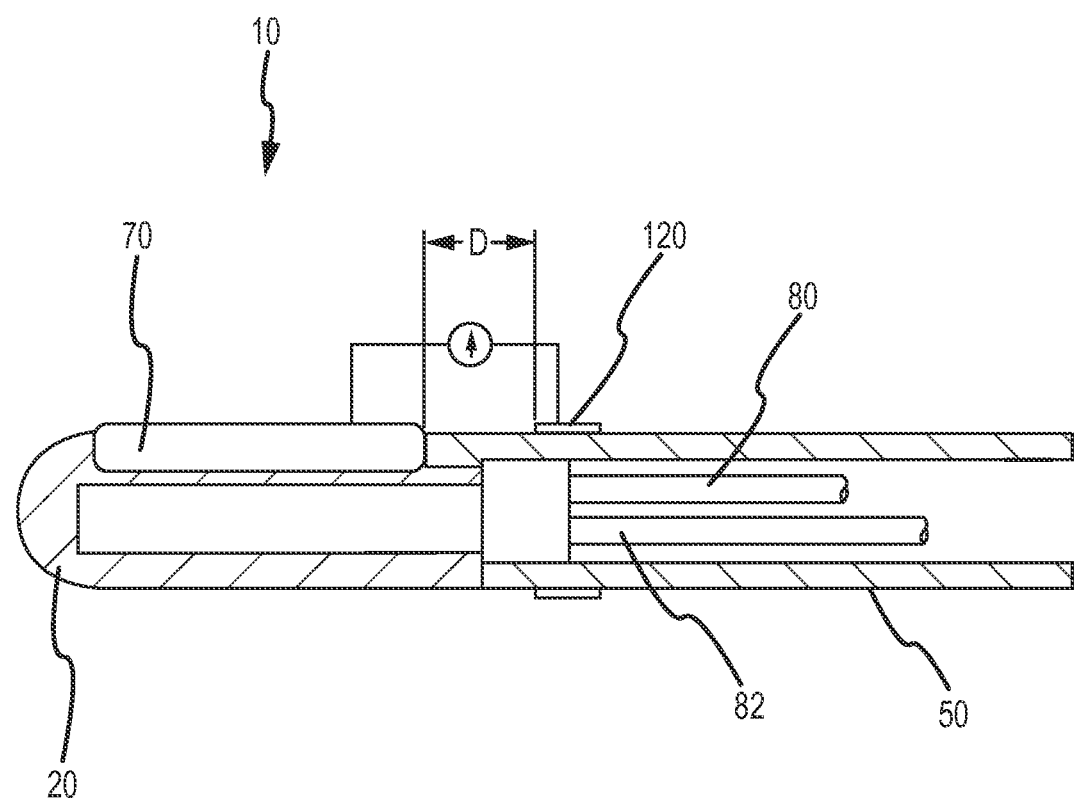
FIG. 22 is a side sectional view of an electrode tip according to an embodiment of the invention.

Another aspect of the invention involves the sensing of contact with tissue and/or the orientation of the electrode tip 10. As generally illustrated in the embodiment shown in FIG. 21, the electrode tip 10 may include an electrode 70, and may additionally include another conductive formation 120, such as a ring or pad. The second conductive formation 120, which may be spaced a known longitudinal distance D from electrode 70, permits the measuring of a signal that is transmitted across the electrode 70 and conductive formation 120, which, in turn, can be used to determine contact with tissue and/or orientation of the electrode tip with respect to such tissue. FIG. 22 provides a side cross-sectional view of an electrode tip of the type generally illustrated in FIG. 21, and includes a form of cooling conduits or lines (e.g., lines 80, 82) to the tip.

Figure 23:
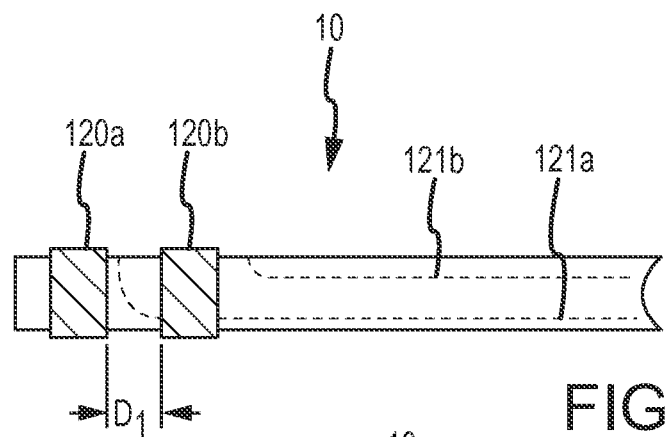
FIG. 23 is a side view of a graphical representation of an electrode tip according to an embodiment of the invention.

FIG. 23 generally illustrates an embodiment of an electrode tip 10 with two conductive formations—comprising two conductive rings 120a, 120b. The conductive rings 120a, 120b may be longitudinally spaced apart at a known distance $D_1$, may comprise a conductive material, and may be connected or coupled to leads 121a, 121b. In an embodiment, the spaced distance $D_1$ may, for example and without limitation, be about 1 mm.

Figure 24:
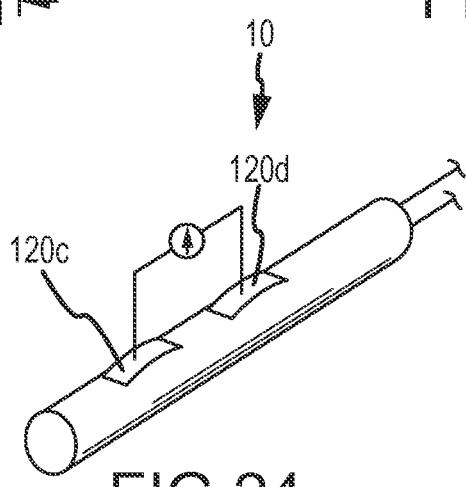
FIG. 24 is a perspective view of an electrode tip according to an embodiment of the invention.
Figure 25:
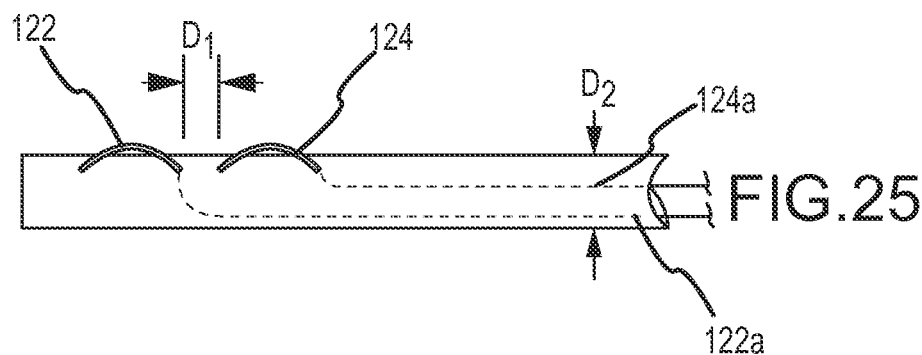
FIG. 25 is a side view of a graphical representation of an electrode tip according to an embodiment of the invention.

In an alternate embodiment, such as generally illustrated in FIG. 24, one or both conductive formations may comprise conductive pads 120c, 120d. FIG. 25 generally illustrates the connection of a first conductive formation 122 and a second conductive formation 124. First and second conductive formations 122, 124 may, respectively, be connected or coupled to separate leads 122a, 124a. In an embodiment, the diameter of the electrode tip, generally represented in FIG. 25 as $D_2$, may be about 3 mm. However, the diameter of the electrode tip is typically only bounded by the diameters associated with the intended application and environment. Consequently, the electrode tip of the present invention may involve other sizes and configurations that are suitable for the intended environments and applications.

Figure 26:
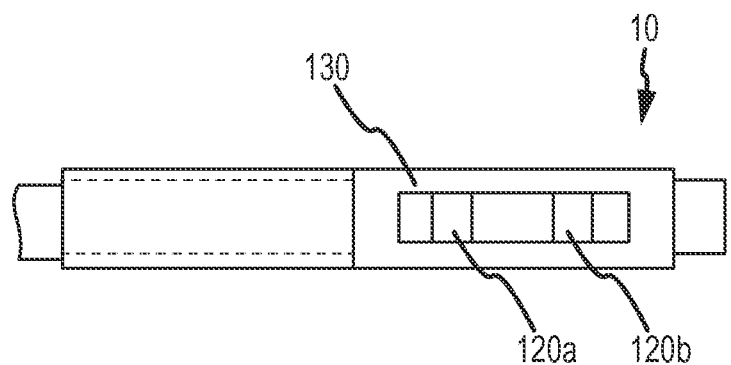
FIG. 26 is a top view of a portion of an electrode tip according to an embodiment of the invention.

FIG. 26 illustrates a variation of an embodiment in which an electrode tip includes two rings 120a, 120b. As generally illustrated only a portion of the rings 120a, 120b are exposed. The remaining portions of the rings 120a, 120b may be coated or otherwise covered, for example, by an electrical insulator or insulating material 130. With such a configuration, the conductive formations, in this instance, rings 120a, 120b, can be used to detect when the electrode tip is in a given conductive relationship. That is, among other things, the conductive formations can detect signals and provide feedback to a user that the electrode tip is in a given contact and orientation with targeted tissue. For example, an electrode tip having such a means for detecting can be rotated and, based upon the signal—which may be processed and displayed remotely (e.g., on a monitor or screen)—a user can ascertain if the ablation portion of the electrode tip is in operative contact or communication with an intended target.

Figure 27:
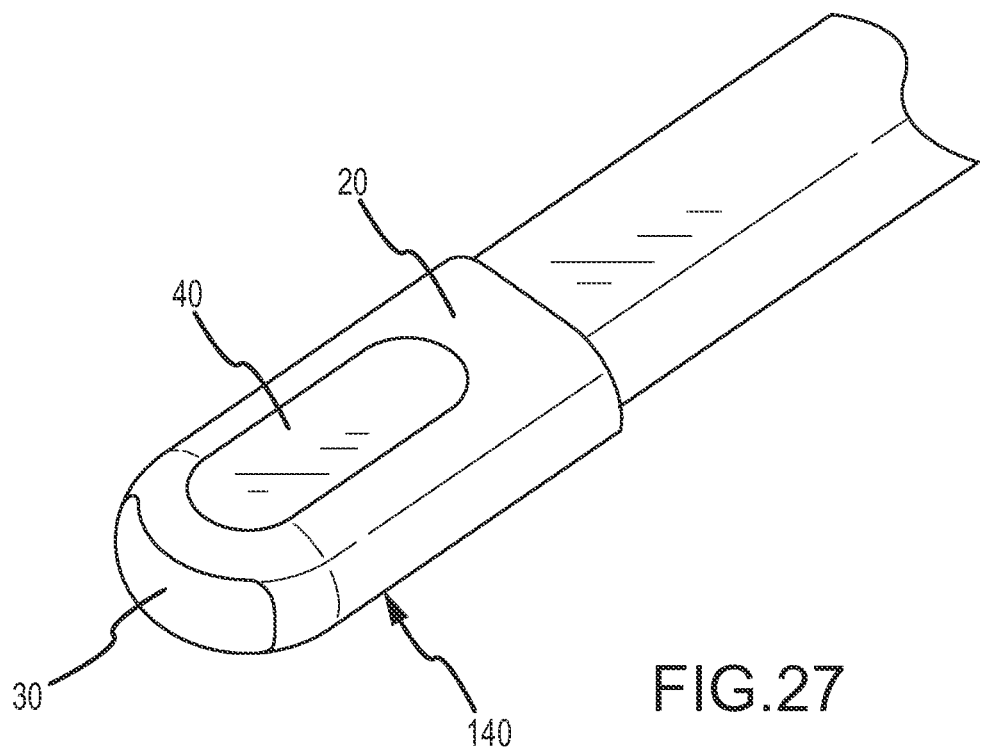
FIG. 27 is a perspective view of an electrode tip according to an embodiment of the invention.
Figure 28:
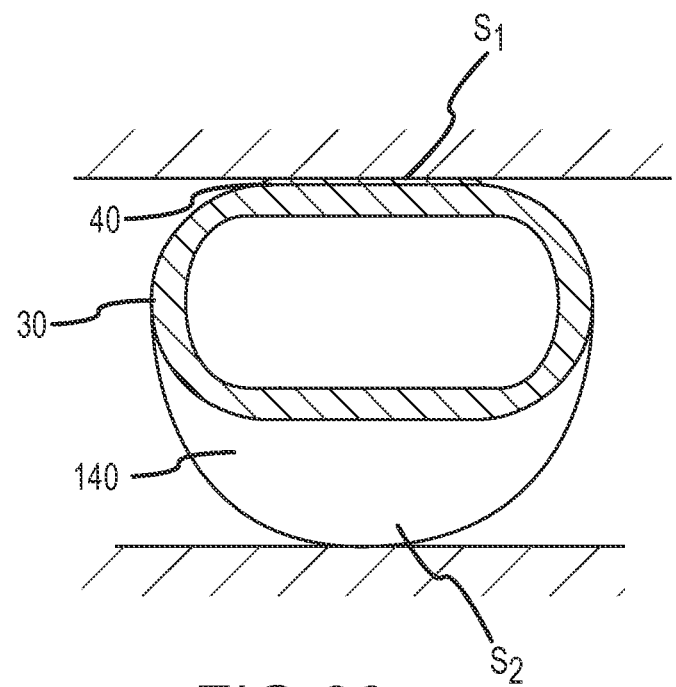
FIG. 28 is a front sectional view of an electrode tip of the type illustrated in FIG. 27.

With some embodiments, the electrode tip may optionally include a means for deflecting or distending adjacent tissue away from a portion of the electrode tip. FIGS. 27 and 28 illustrate an example of such a means for deflecting or distending adjacent tissue away from a portion of the electrode tip in the form of a balloon or bladder 140 that may be selectively filled (e.g., with a gas or fluid) and/or evacuated or collapsed. Depending upon the application and configuration, the associated balloon or bladder 140 may comprise a flexible, rigid, or semi-rigid material.

Figure 29:
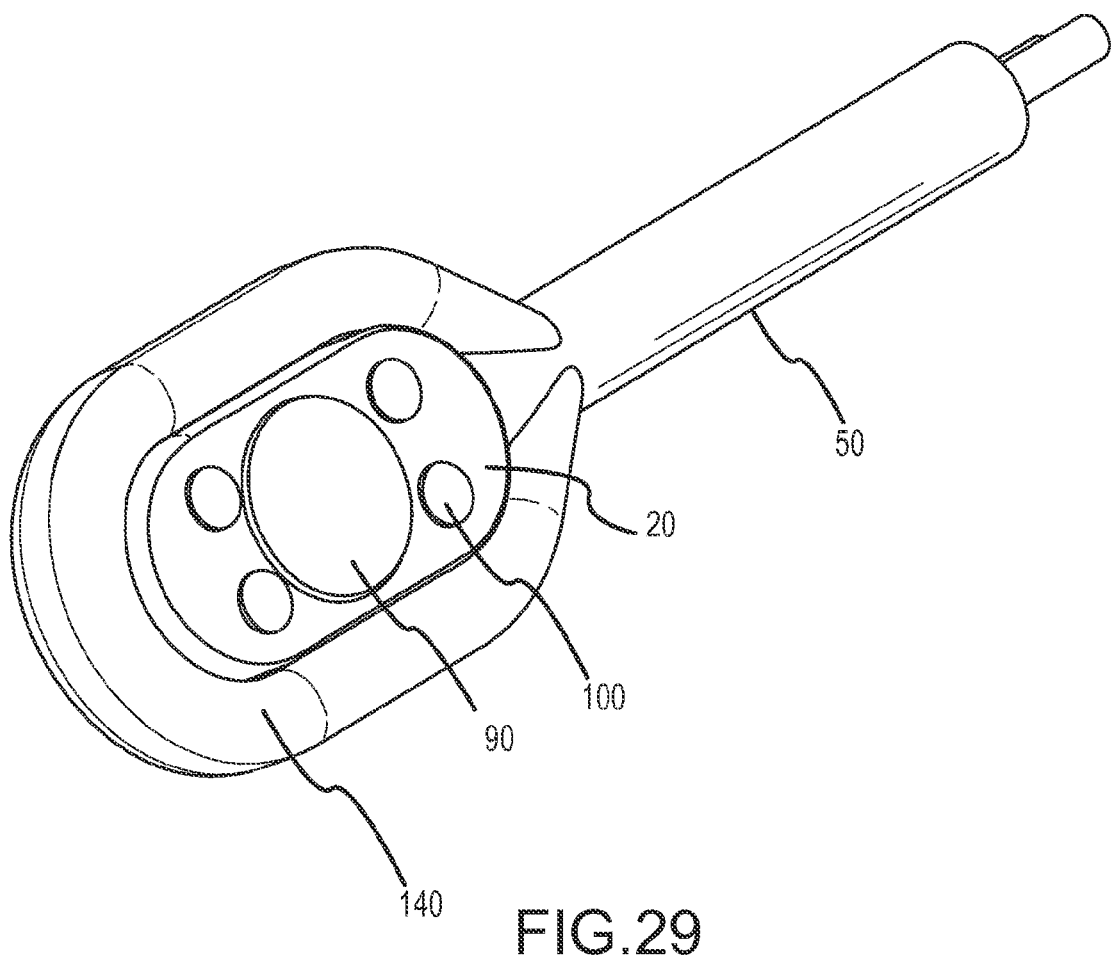
FIG. 29 is a perspective view of an electrode tip according to an embodiment of the invention.
Figure 30:
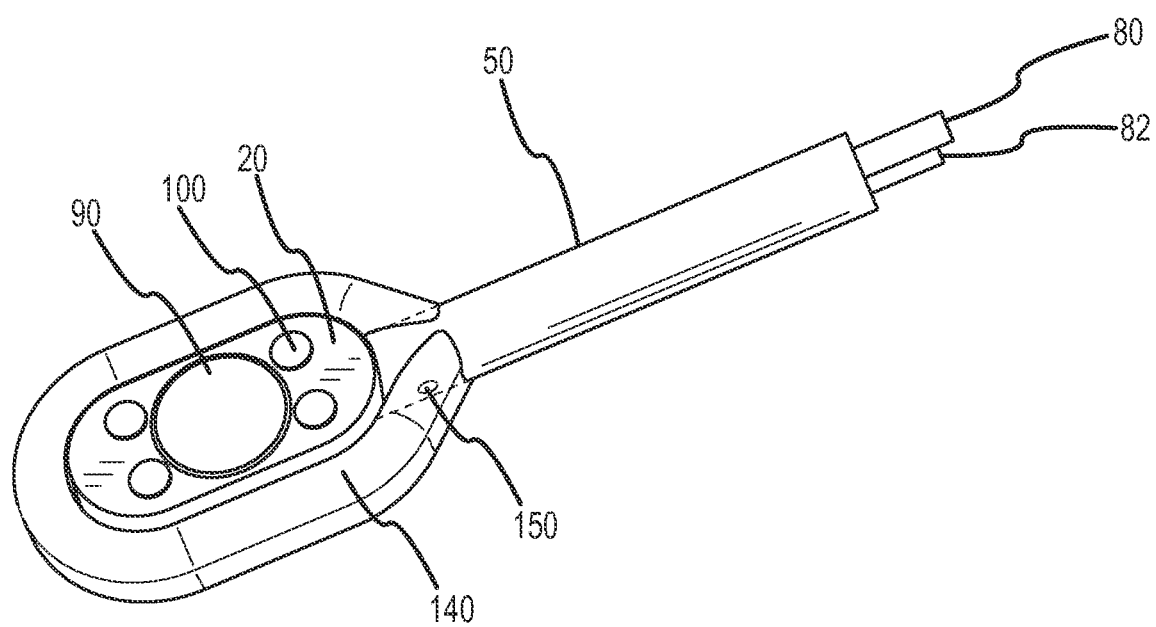
FIG. 30 is a rotated perspective view of the electrode tip illustrated in FIG. 29.
Figure 31:
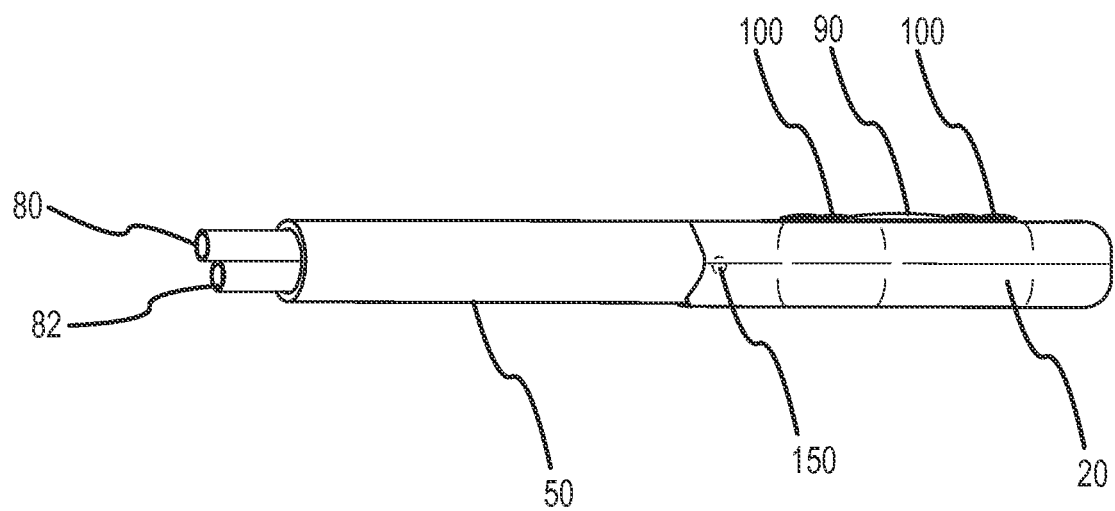
FIG. 31 is a side view of the electrode tip illustrated in FIG. 29.

FIGS. 29-31 generally represent another embodiment of an electrode tip that includes a means for deflecting or distending adjacent tissue away from a portion of the electrode tip. Among other things, the means for deflecting or distending adjacent tissue away from a portion of the electrode tip may increase the distance of the electrical pathway to help protect adjacent tissue or structures from unintended damage due to the supply of energy or heat from the electrode tip. As generally shown, a side-firing electrode tip of the type previously shown and discussed in connection with FIGS. 16-20, may include a paddle-like carrier 20 and may include at least one balloon or bladder 140 that may surround or circumscribe the ablation region of the electrode tip (e.g., a central electrode 90 and a plurality of relatively smaller button electrodes 100) and comprise means for deflecting or distending adjacent tissue away from a portion of the electrode tip. Depending upon the desired application and configuration, the balloon or bladder 140 may extend in a direction opposing the direction of ablation treatment from the electrode tip, which can help improve the contact or operative communication of the electrodes with an intended treatment site. As generally shown in FIG. 30, one or more supply openings or access ports 150 may be in internal communication with the balloon or bladder 140, and may provide for the controllable filling and/or evacuation of a gas or fluid from all or a portion of the balloon or bladder 140. Supply lines or conduits for such openings or ports 150 can extend through an associated catheter 50 to one or more remote supply source and/or receiving unit.

Figure 32:
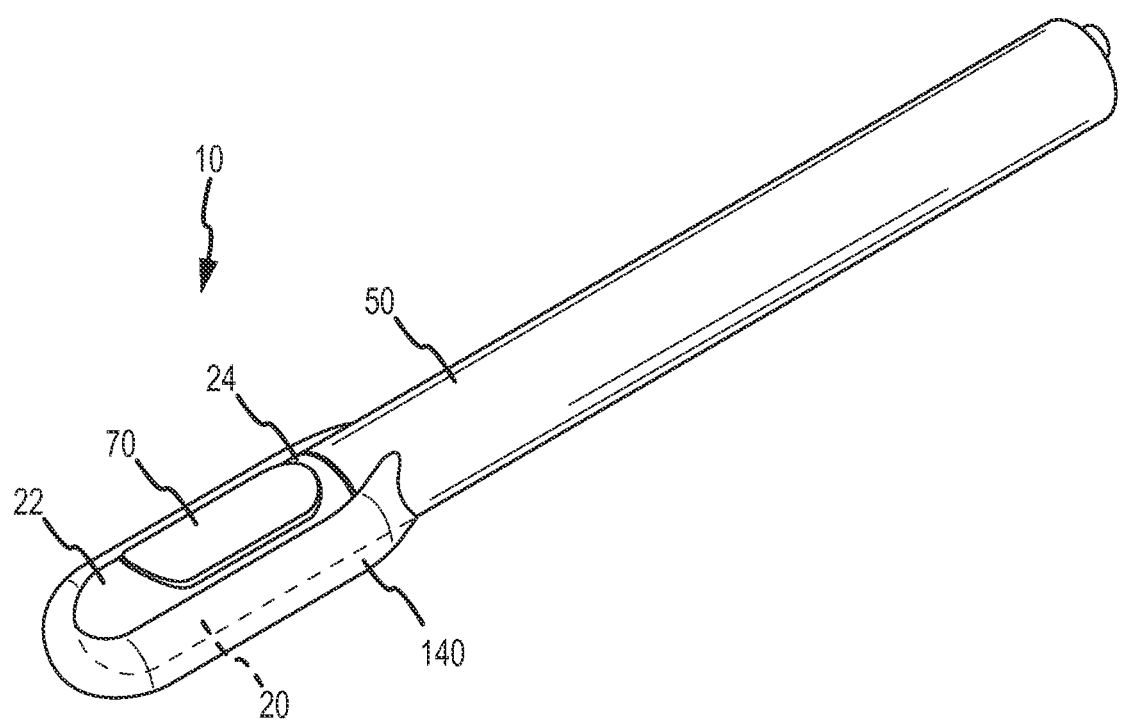
FIG. 32 is a perspective view of an electrode tip according to an embodiment of the invention.

FIG. 32 generally illustrates an electrode tip 10 according to another embodiment of the invention. As generally shown, electrode tip 10 may include an electrode 70 and an electrode carrier 20 having a distal portion 22 with a hemispherical portion, and a proximal portion 24. Electrode tip 10 may be connected to a portion of a catheter 50, and may further include a balloon or bladder 140 of the type previously disclosed.

Figure 33:
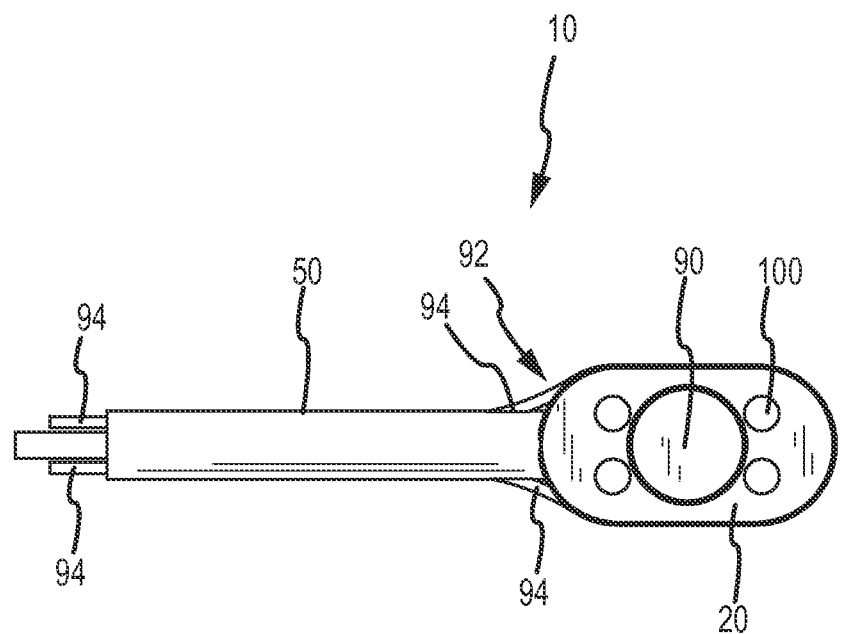
FIG. 33 is a front view of an electrode tip according to an embodiment of the invention.
Figure 34:
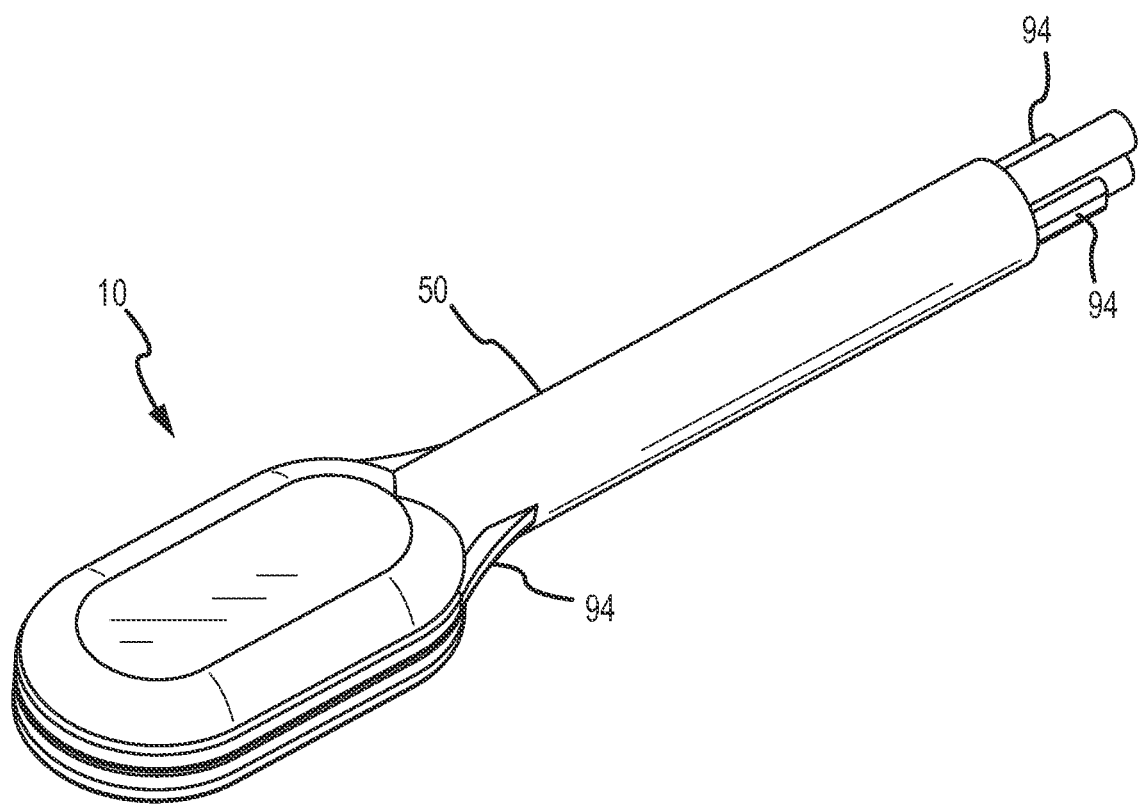
FIG. 34 is a rear perspective view of the electrode tip of FIG. 33.
Figure 35:
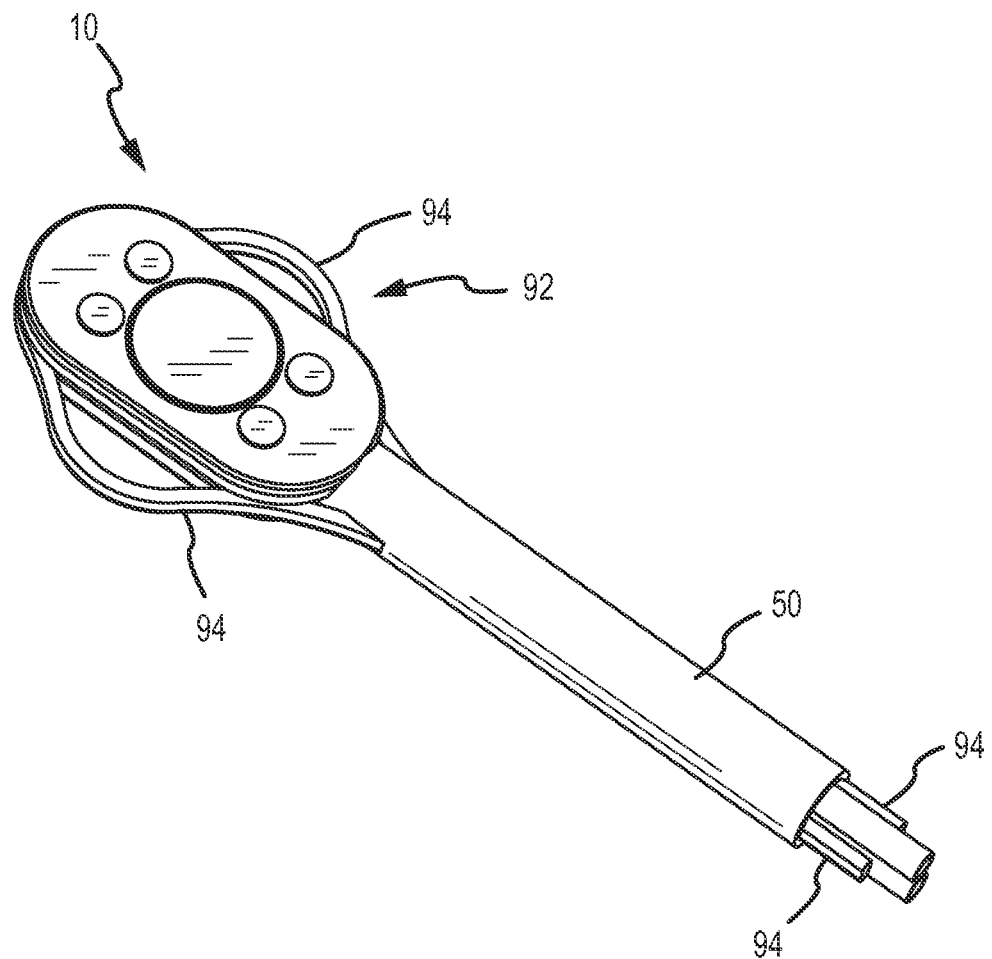
FIG. 35 is a front perspective view of the electrode tip of FIG. 33, shown with a mechanical distention member in a deployed configuration.
Figure 36:
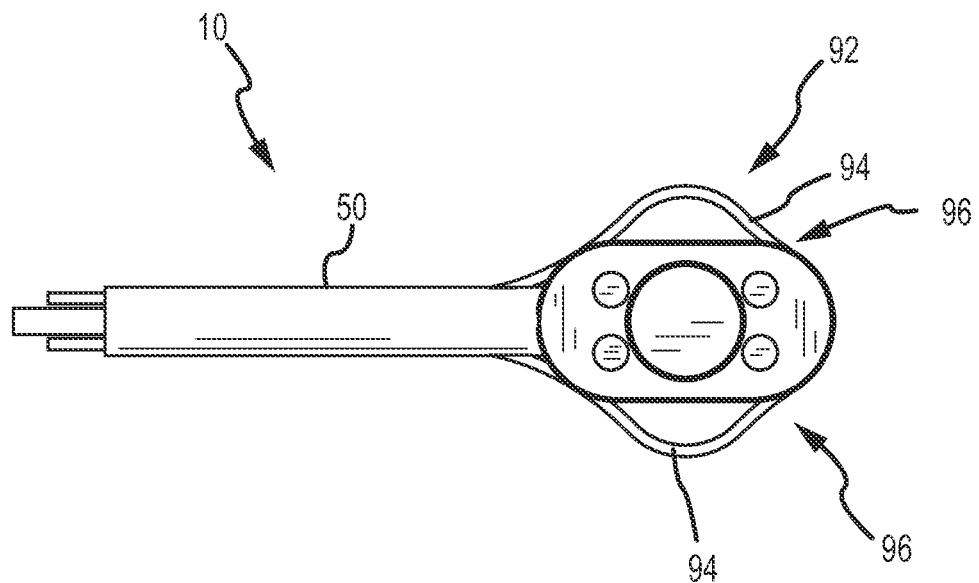
FIG. 36 is a front view of the electrode tip of FIG. 33, shown with a mechanical distention member in a deployed configuration.
Figure 37:
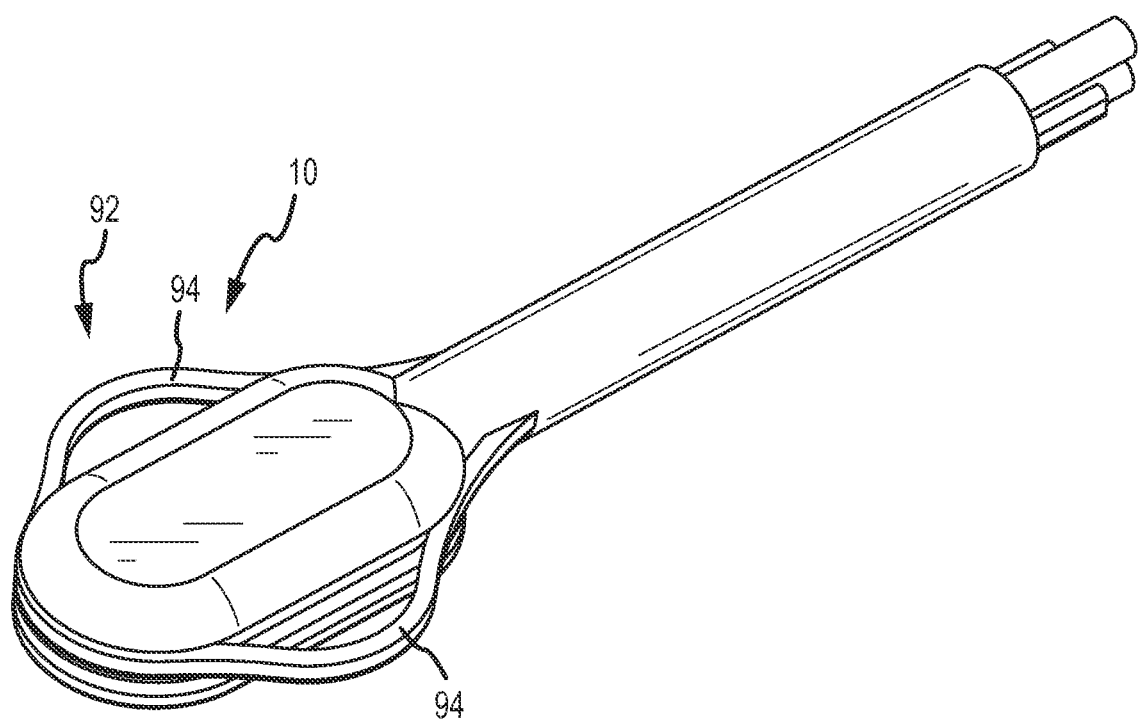
FIG. 37 is a rear perspective view of the electrode tip of FIG. 33, shown with a mechanical distention member in a deployed configuration.

For other embodiments, the means for deflecting or distending adjacent tissue away from a portion of the electrode tip may comprise one or more small-diameter wires, plastic extensions, or other formations that can be deployed and reduced or retracted as necessary or desired. An example of such a configuration is disclosed in FIGS. 33-37. FIGS. 33 and 34 generally illustrate an electrode tip 10 in a non-deployed configuration, while FIGS. 35-37 generally illustrate the electrode tip 10 in a deployed configuration. As shown in the views of the illustrated embodiment, the electrode tip 10 may include an electrode carrier 20, an electrode 90, and a mechanical distention member 92. By way of example, without limitation, the electrode tip 10 may also optionally include one or more additional electrodes, such as a plurality of relatively smaller round button electrodes 100.

The mechanical distention member 92 may, for example, comprise one or more wires or leads 94 that may be secured at a position (see e.g., positions 96 shown in FIG. 36) on or about the electrode tip 10 such that portions of the wires or leads 94 may extend outwardly from the tip 10 to provide a means for separation from adjacent tissue or surfaces.

The foregoing means for deflecting or distending adjacent tissue or surfaces away from a portion of the electrode tip can, among other things, be configured to further separate ablation portions of the electrode tip from tissue or areas of the patient that are not intended to be treated; provide additional stability to the electrode tip relative to the area to be treated; and/or provide improved or additional contact force for the ablation portions of the electrode tip with respect to areas being treated (see, e.g., the surface generally designated as $S_1$).

Moreover, for some embodiments, including those previously described, the means for deflecting or distending adjacent tissue away from a portion of the electrode tip may be filled with a fluid or gas, and may be additionally used to help cool adjacent tissue (e.g., tissue associated with the surface generally designated in FIG. 28 as $S_2$), which may reduce the likelihood of collateral damage to unintended tissue. In embodiments, the fluid or gas may comprise, without limitation, saline, sterile water, or air.

Figure 38:
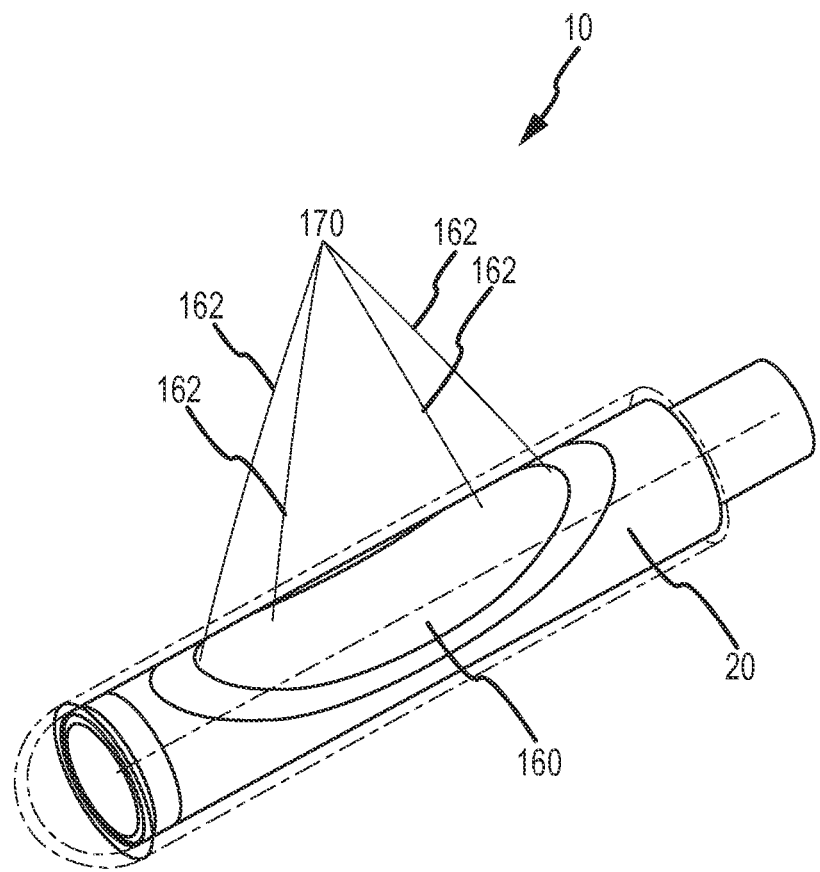
FIG. 38 is a perspective view of an electrode tip according to an embodiment of the invention, shown with a portion of the distal end in phantom.

As previously noted, while various features and embodiments of the invention are generally discussed in connection with electrode tips employing radio frequency (RF) energy, the present invention is not limited to a single type of energy source. By way of example, without limitation, FIG. 38 generally illustrates an electrode tip that includes a transducer element 160, which may comprise one or more ultrasonic transducers. Typically, each transducer will have a line of focus (generally represented by lines 162). When a plurality of transducers are included in an electrode tip (i.e., with one or more transducer elements), the transducers may be positioned and configured so that their lines of focus will converge at a focal point 170. However, some embodiments, may include multiple focal points and, further, may include a focal region comprised of distributed foci.

Figure 39:
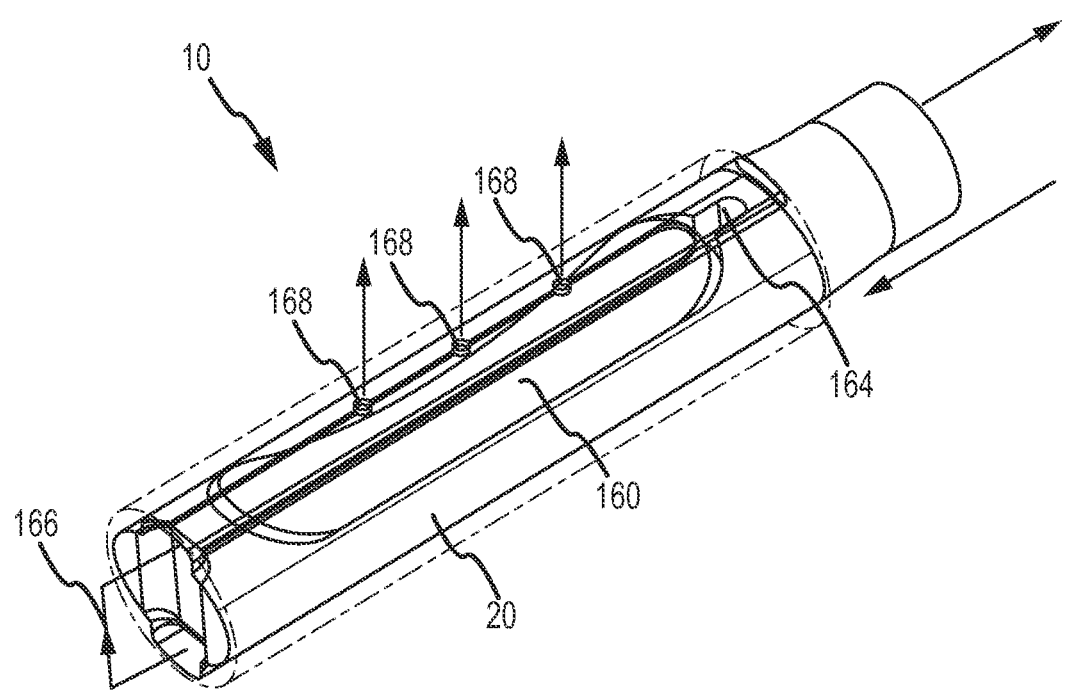
FIG. 39 is a perspective view of a portion of an electrode tip according to an embodiment of the invention.

FIG. 39 generally discloses an embodiment of a portion of an electrode tip 10 that includes a transducer element 160, an electrical access port 164, a coolant path 166 (which may follow the flow path indicated by the arrows), and one or more ports or openings 168 that are in communication with the coolant path and permit external release of a coolant about the transducer element 160 and possibly other portions of electrode tip 10. Further, in an embodiment, electrical access port 164 may, for example, provide access for electrical lines and may be potted closed. If desired, transducer element 160 may be bonded into electrode carrier 20. For some embodiments, the full active surface face of the transducer element may be exposed to a coolant, such as saline, which may be bled off through a plurality of ports or openings 168.

Figure 40:
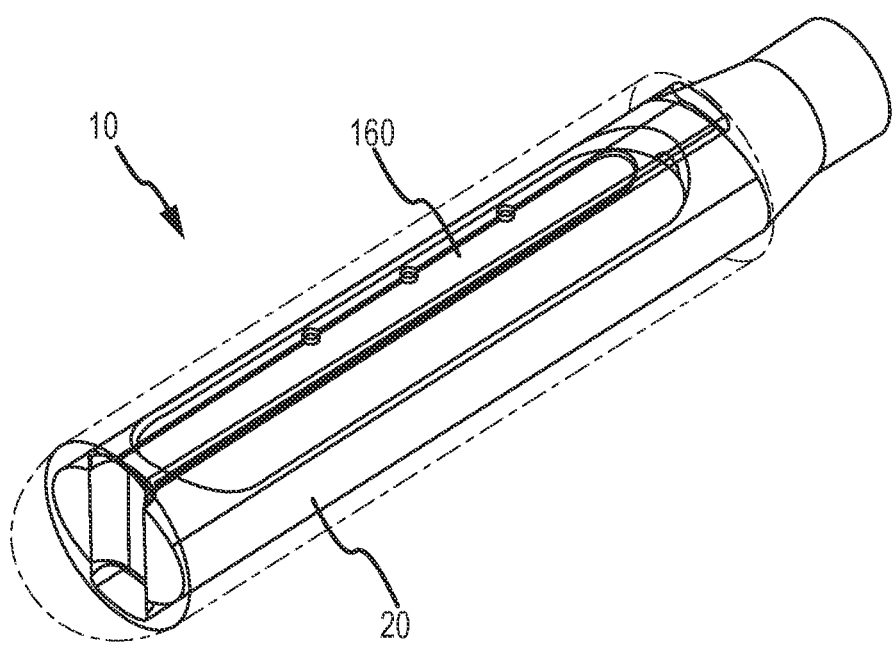
FIG. 40 is a perspective view of an electrode tip according to an embodiment of the invention, shown with a portion of the distal end in phantom.
Figure 41:
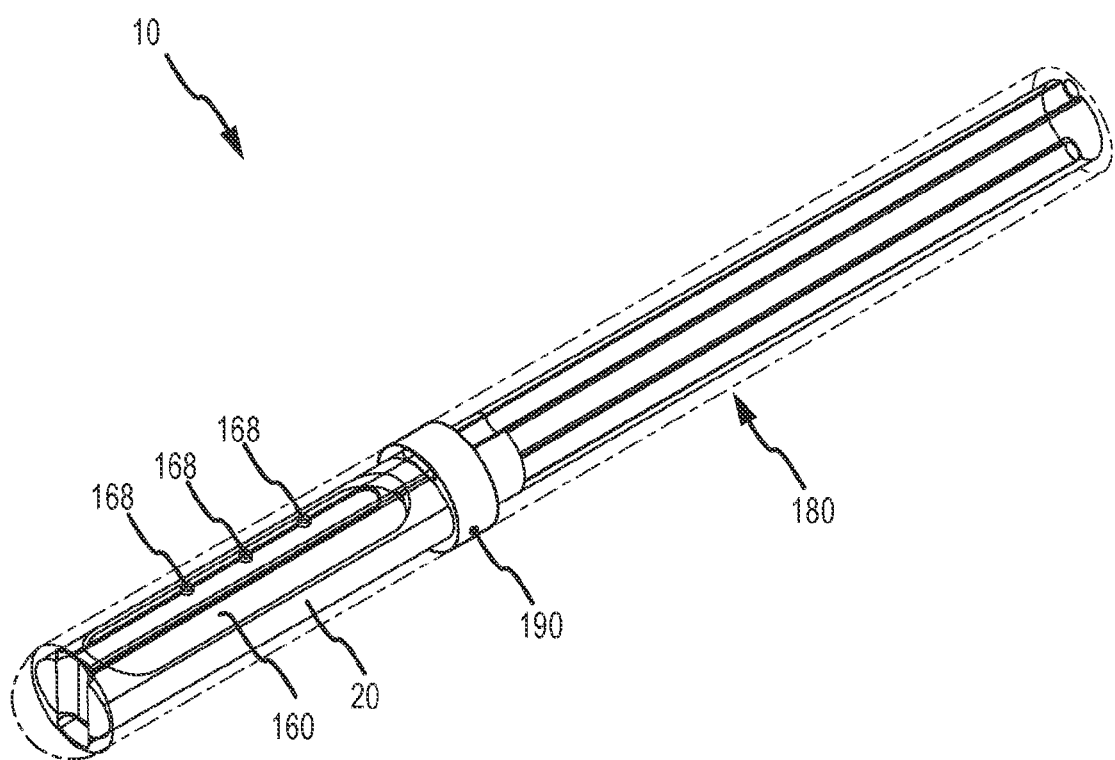
FIG. 41 is a perspective view of an electrode tip according to an embodiment of the invention, shown with a manifold and with a portion of the distal end in phantom and a portion of the associated tube in transparent form.
Figure 42:
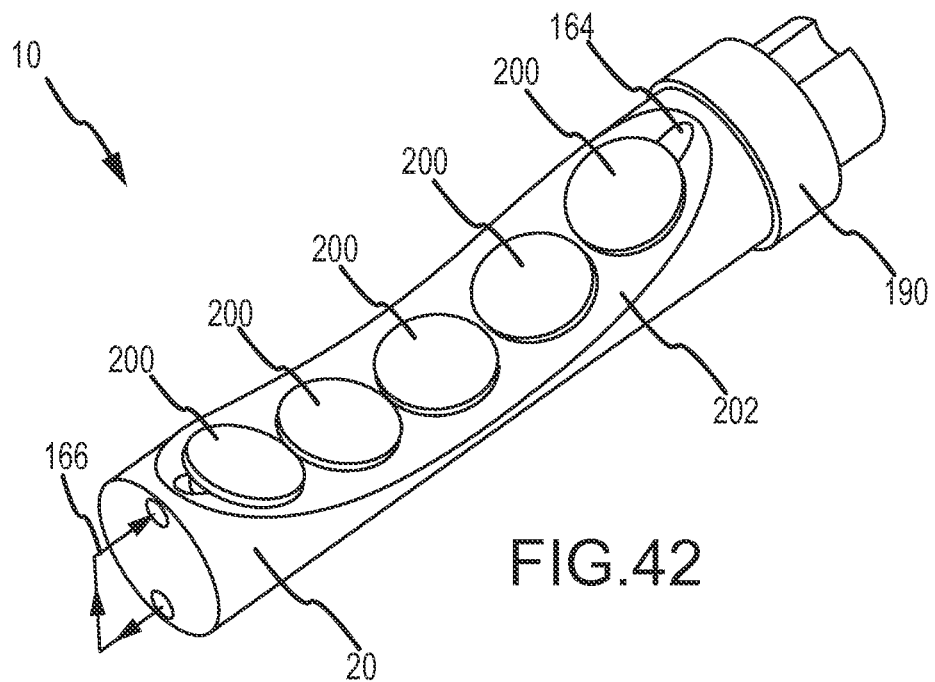
FIG. 42 is a perspective view of a portion of an electrode tip according to an embodiment of the invention.
Figure 43A:
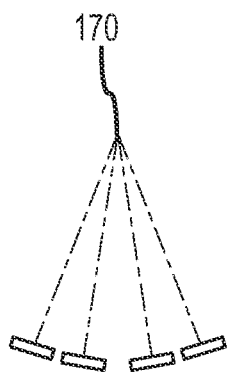
FIG. 43A is representation of a focal point associated with multiple transducers.
Figure 43B:
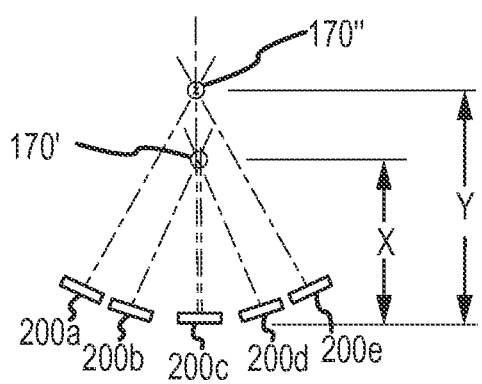
FIG. 43B is representation of multiple focal points associated with multiple transducers.

Additional embodiments of an electrode tip 10 are included in FIGS. 40-42. FIG. 40 generally illustrates an embodiment of an electrode tip 10 that includes a substantially flat transducer element 160. FIG. 41 generally illustrates an electrode tip 10 with a transducer element 160 according to an embodiment of the invention. The electrode tip 10 is shown including a plurality of openings 168 and a manifold 190. The electrode tip 10 is shown connected to a multi-lumen tube, which is shown with a transparent outer surface to better illustrate several lumens 180 in communication with the electrode tip 10. FIG. 42 generally illustrates an electrode tip with an electrode element comprised of a plurality of transducers 200. As shown, the transducers 200 may be provided in the form of a curved linear array, which may, for example, be configured on a curved surface 202. FIG. 43A illustrates, in a non-limiting manner, how a plurality of transducers 200 may be configured such that their lines of focus will converge at a focal point or region 170. FIG. 43B represents an embodiment in which a plurality of transducers 200 are configured such that their lines of focus, the operation of activation/power which may be selectively controlled, provide a first focal point 170' at a first distance X, and a second focal point 170" at a second distance Y that is farther away from the transducer element. For example, as generally illustrated in FIG. 43A, a first intensity of power may be directed to the first focal point 170' by activating transducers 200b and 200d. It is possible for a second, higher intensity of power to be directed to the same first focal point 170' by additionally activating transducer 200c. A similar power/application control may be associated with focal point 170". Further, for other embodiments, additional focal points may be provided in connection with the configuration of the associated transducer element or elements. While various transducer-related embodiments are illustrated in FIGS. 38-42, it is important to note that various additional features discussed in connection with other embodiments may also be included with and/or incorporated into the transducer-related embodiments. For example, without limitation, the transducer-related embodiments may also include similar means for cooling and/or means for deflecting or distending surrounding tissue.

Figure 44:
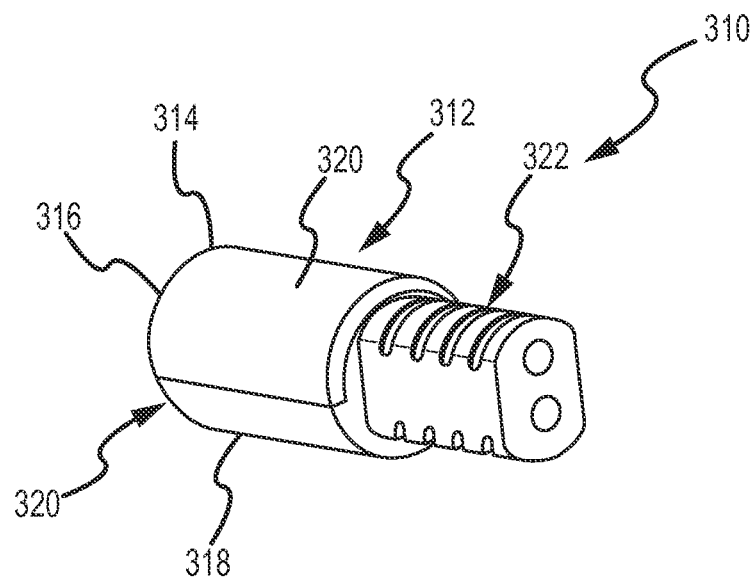
FIG. 44 is a perspective view of an electrode in accordance with an alternate embodiment of the present invention.

FIG. 44 illustrates an electrode 310 according to an alternate embodiment of the invention. Electrode 310 may be designed for use as a radiofrequency (RF) ablation electrode, although alternate types of energy sources may be used such as ultrasound, laser, high frequency ultrasound or any others that are typically used for performing ablation procedures. With reference to FIG. 44, ablation electrode 310 defines an electrode body 312. The electrode body 312 includes an outer surface 314, a top portion 316 and a bottom portion 318. In accordance with one embodiment of the present invention, top portion 316 further includes an insulated member or portion 320. Bottom portion 318 provides an electrically conductive surface and is adapted to direct energy unidirectionally towards target tissue. Accordingly, electrode 310 is supplied with ablative energy throughout the electrically conductive surface of the electrode. The ablative energy radiates or exits the electrode throughout the entire electrode but is absorbed by the insulated member or portion 320 that is in contact with the electrically conductive surface. Accordingly, the ablative energy is unidirectional.

Electrode body 312 can be generally cylindrical in shape, as shown in FIG. 44. Body 312 may also be formed in other shapes and/or configurations, such as in an elliptical shape or flat shape, which provides more surface area of body 312 in contact with the target tissue. The additional surface contact of the electrode body 312 with the target tissue prevents the body 312 from having a tendency to roll along the ablative surface and alter the position of the insulated portion or member 320. Accordingly, various embodiments and alternate designs of electrode body 312 are contemplated within the scope of the present invention. It should be noted that "top" and "bottom" are only used for the purposes of identifying orientation and it is further recognized that each of these terms may be interchangeable depending on the orientation of the electrode body 312 in connection with the target tissue during an ablation procedure.

Insulated member or portion 320 may be comprised of a polymer, which further may be thermally and/or electrically nonconductive, and may protect tissue from exposure to the electrical energy of the ablative surface of the electrode. Moreover, the insulated member 320 may be further comprised of a reduced thermally conductive polymer. A reduced thermally conductive material is one with physical attributes that decrease heat transfer by about 10% or more, provided that the remaining structural components are selected with the appropriate characteristics and sensitivities to maintain adequate monitoring and control of the process. One reduced thermally conductive material may include polyether ether ketone ("PEEK"). Further examples of reduced thermally conductive materials useful in conjunction with the present invention include, but are not limited to, HDPE, polyimides, polyaryletherketones, polyetheretherketones, polyurethane, polypropylene, oriented polypropylene, polyethylene, crystallized polyethylene terephthalate, polyethylene terephthalate, polyester, polyetherimide, acetyl, ceramics, and various combinations thereof.

Comparably, bottom portion 318 may be comprised of an electrically conductive surface, such as those used in traditional electrodes, to direct energy in a downward direction towards target tissue. Examples of electrically conductive material include gold, platinum, iridium, palladium, stainless steel, and various mixtures and combinations thereof.

Figure 45:
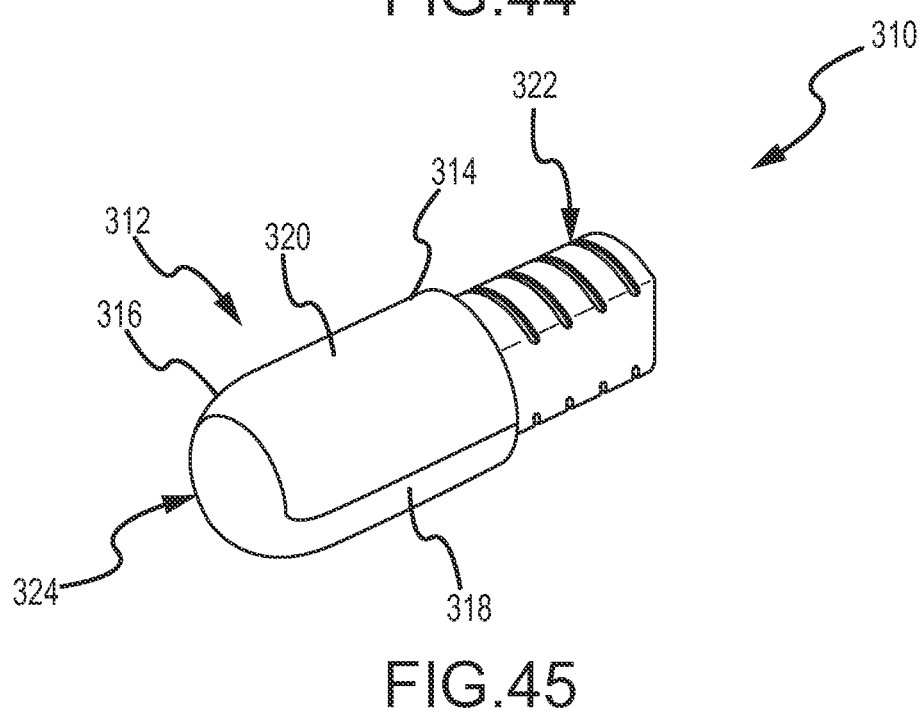
FIG. 45 is an alternate perspective view of the electrode as shown in FIG. 44.

As shown in FIGS. 44 and 45, electrode 310 is an integral unitary member formed by the connection or coupling of top portion 316 including insulated portion 320 and bottom portion 318. Accordingly, insulated portion/member may be snap-fit into place with bottom portion 318, molded in connection with bottom portion 318, i.e. injection molding, or manufactured using various other methods to ensure that electrode 310 is and remains a unitary structure for connection with a catheter shaft for insertion through an access device or introducer (not shown). Moreover, electrode 310 of the present invention further includes a connection portion 322, provided on the proximal end of electrode body 312, adapted for connecting electrode 310 to a catheter shaft (not shown). Connection portion 322 may be configured in accordance with principles known in the art and traditionally used for connecting electrodes and/or electrode tips to catheter shafts to form a catheter assembly.

As shown in FIG. 45, electrode 310 further includes body 312 having a distal end or tip 324. In accordance with one embodiment of the present invention, distal end or tip 324 may be hemispherical or semispherical in shape, although alternate shapes of distal end 324 are contemplated by the present invention. As shown in FIG. 45, hemispherical end 324 may be comprised of an electrically conductive material. Accordingly, the end portion continues to direct ablative energy to the target tissue and/or surround surfaces.

Figure 46:
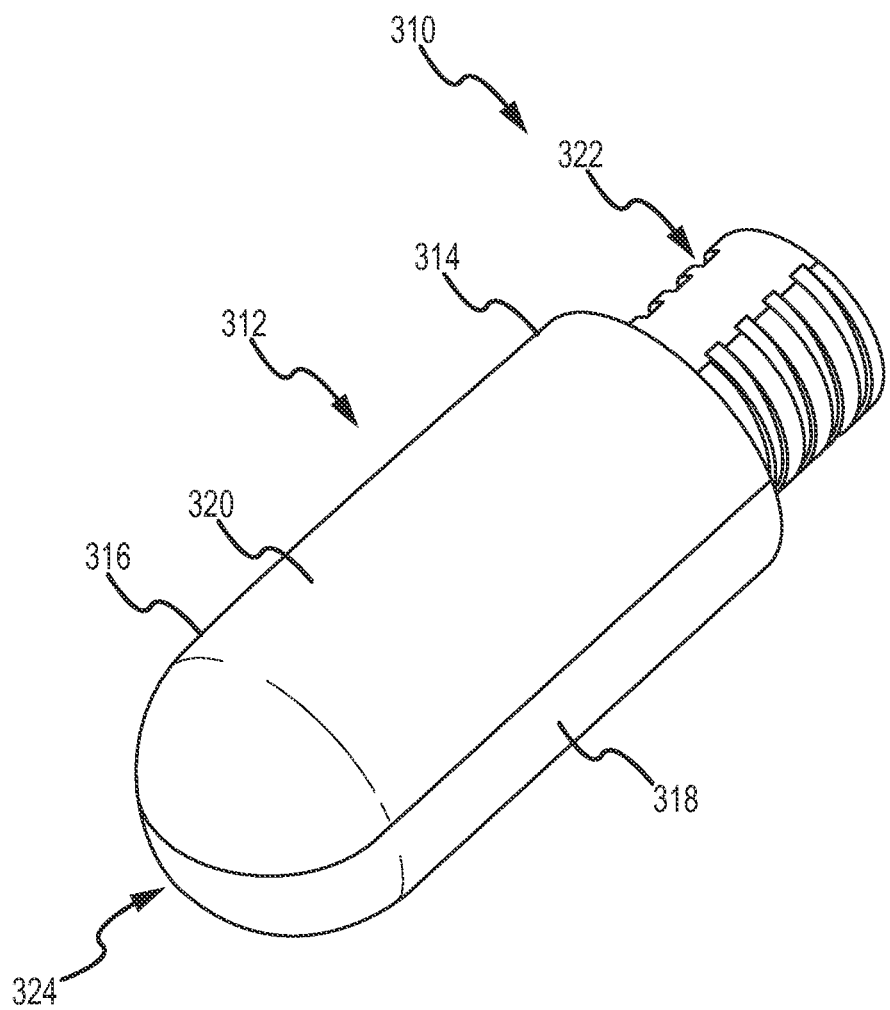
FIG. 46 is a perspective view of an electrode in accordance with an alternate embodiment of the present invention.

FIG. 46 further provide an alternate embodiment of the present invention wherein top portion 316 of electrode body 312 is substantially or entirely comprised of insulated material, therein providing a substantially or fully insulated top portion 316. Moreover, the upper portion of distal end 324 may be insulated and comprise a thermally and/or electrically nonconductive material, as well as potentially a reduced thermally conductive material. As previously described above, the insulated electrode tip may be formed using various methods known to one of ordinary skill in the art, such as injection molding the insulating member with the electrically conductive material of bottom portion 318. As can be seen in FIG. 44-46, the present invention contemplates alternate embodiments of electrode 310 wherein top portion 316 of body 312 is either partially or completed provided by an insulated member 320. Alternate configurations or patterns of insulated member 320 may be used depending on the design and intended use of the electrode.

Figure 47:
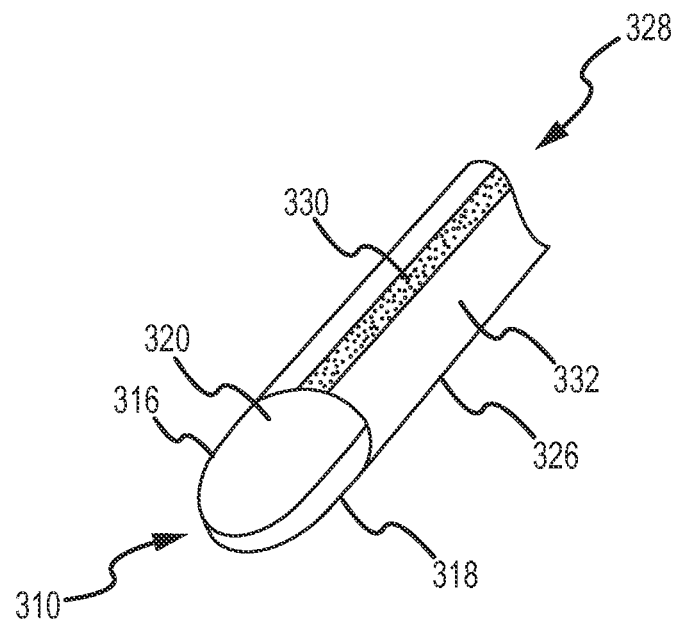
FIG. 47 is a perspective view of a catheter assembly including electrode of the type generally shown in FIG. 46.

FIG. 47 further provides electrode 310, as shown in FIG. 46, in connection with a catheter shaft 326, to form catheter assembly 328. In accordance with an embodiment of the present invention, catheter shaft 326, may include an orientation marker 330, such as an extruded stripe along the outer surface 332 of catheter shaft 326. Orientation marker 330 may, also, for example, be comprised of a fluoroscopic material, such that the orientation and position of shaft 326 may be determined with reference to the position of electrode 310. In addition, alternate embodiments may provide one or more orientation markers via a number of methods, such as extrusion or incorporation of a fluoroscopic material on catheter shaft 326. In general, it is desirable to make sure marker 330 is clearly visible by the user in order to reference the orientation of catheter shaft 326, while at the same time, ensuring that marker 330 does not interfere with the overall size and/or profile of catheter shaft 326. In an embodiment, orientation marker 330 may be aligned with electrode 310 such that top portion 316 which includes insulated member 320 is on the same plane orientation as the orientation marker 330. The inclusion of orientation marker 330 ensures that the user knows which surface of the electrode 310 is the top portion 316 and includes the insulated portion or member 320. Orientation marker 330 aids in ensuring that the ablative energy is direction towards the target tissue and not towards the surrounding tissue, such as the pericardial sac and/or lungs.

Figure 48A:
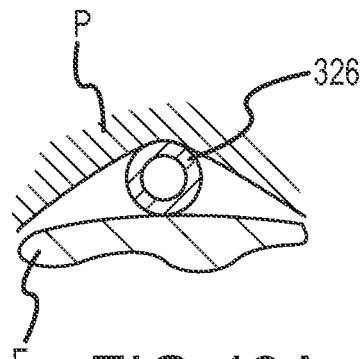
FIG. 48A is a front cross-sectional view of a traditional catheter shaft positioned between the pericardial sac and the epicardial wall of the heart.
Figure 48B:
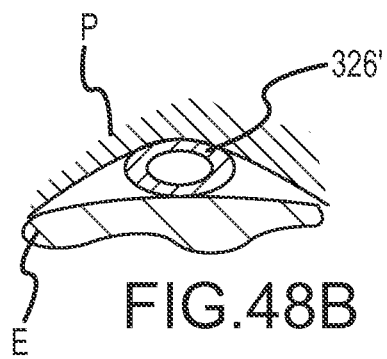
FIG. 48B is an front cross-sectional view of a catheter shaft in accordance with an embodiment of the present invention.

FIGS. 48A and 48B shows cross-sectional view of a catheter shaft 326 as inserted between the pericardial sac (P) and epicardial surface (E) of the heart during the performance of an ablative procedure on the surface of the heart. In particular, FIG. 48A provides a cross-sectional view of traditional catheter shaft that is cylindrical in shape. In comparison, FIG. 48B provides a cross-section view of a catheter shaft in accordance with an embodiment of the present invention. FIG. 48B provides a catheter shaft 326' that is extruded to and has a substantially elliptical cross-sectional shape, or non-cylindrical shape. Such configurations can be used to help prevent the catheter shaft from easily rolling off or along a targeted ablative surface. As a result, the orientation and direction of an electrode 310 as coupled to a substantially elliptical catheter shaft 326 can be readily controlled once inserted into through the access device or introducer and placed into position. This substantially elliptical shape helps ensure that insulated portion 320 and ablative surface, which may be provided by bottom portion 18, are adequately oriented within a target space. Moreover, electrode 310 may be provided in a substantially elliptical cross-sectional shape to reflect the shape of catheter shaft 326' and ensure a smooth transition between electrode 310 and catheter shaft 326'.

Figure 49:
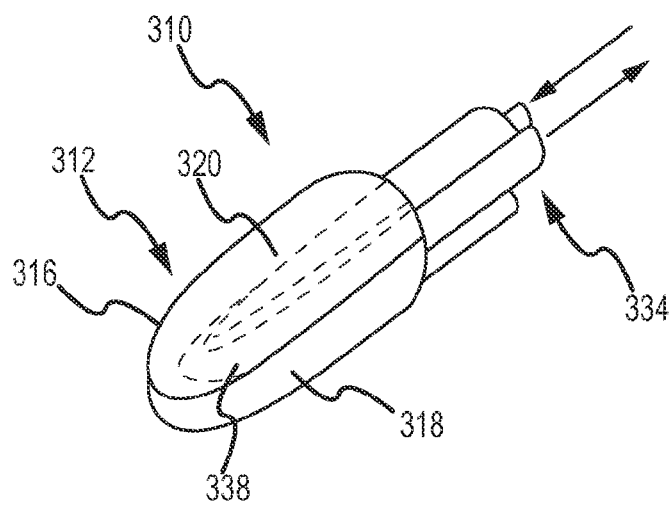
FIG. 49 is perspective view of an electrode in accordance with an alternate embodiment of the present invention, including a cooling system shown in phantom.
Figure 50A:
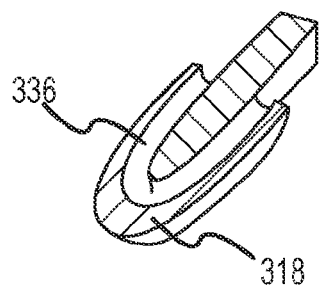
FIGS. 50A-50C are perspective views of components of an electrode of the type generally shown in FIG. 49.
Figure 50B:
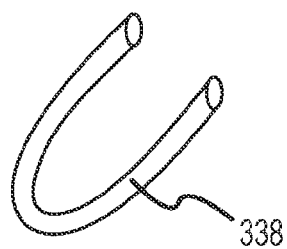
Figure 50C:
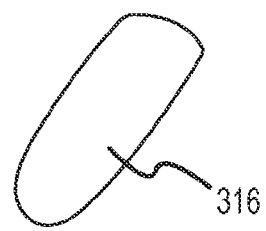
Figure 51:
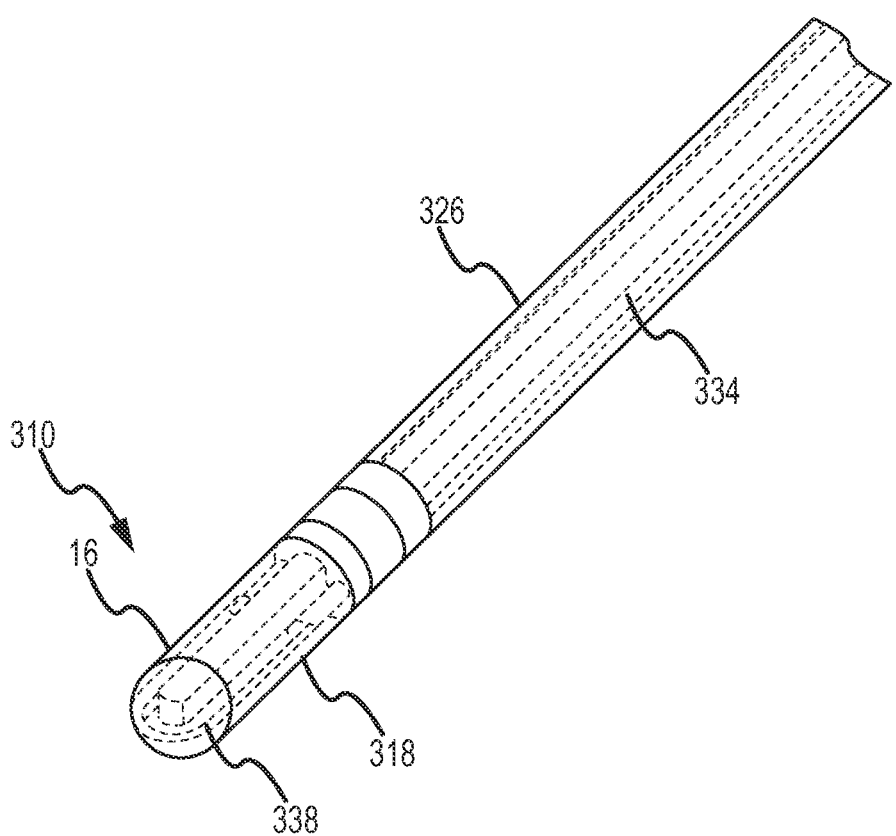
FIG. 51 is a perspective view of a catheter assembly including the electrode as shown in FIG. 49.

FIGS. 49-51 show an electrode 310 in accordance with an alternate embodiment of the present invention. Electrode 310 includes a means for cooling at least a portion of the electrode 310, for example, as shown in phantom in FIG. 49. In particular, electrode 310 as shown in FIG. 49 may include one or more fluid lines, passageways and/or conduits 334 for transmitting fluid to and/or from the electrode 310. The means for cooling may further include a closed-loop cooling system for cooling a portion of the electrode body 314. FIGS. 50A-50C provide perspective views of the components of the cooling electrode 310. FIG. 50A shown bottom portion 318 having a recessed groove 336 for receiving cooling member 338, for example, as generally shown in FIG. 50B. Cooling member 338 may further include a tubing-like material or configuration therein providing an inner lumen allowing for the biocompatible fluid (e.g. saline) to pass through and cool electrode body 312. Although shown in a single orientation through bottom portion 318 of electrode body 312, cooling member 338 may be configured in alternate ways to provide a means for cooling at least a portion of the electrode 310. FIG. 50C further provides the top portion 316 of electrode body 312. Top portion 316, as shown in accordance with this embodiment, may be partially or fully insulated, or may include a insulated portion or member 320 that is only part of top portion 316. FIG. 51 further provides a perspective view of electrode 310 as shown in FIGS. 49-50C. Electrode 310, as shown in FIGS. 49-50C, is connection with catheter shaft 326 therein providing fluid lines to and from the electrode 310 to cool the outer surface 314 of electrode body 312.

Figure 52:
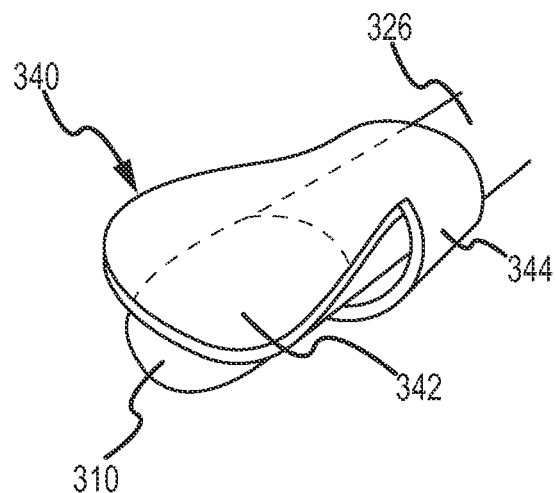
FIG. 52 is a top perspective view of an electrode assembly in accordance with another embodiment of the present invention.
Figure 53:
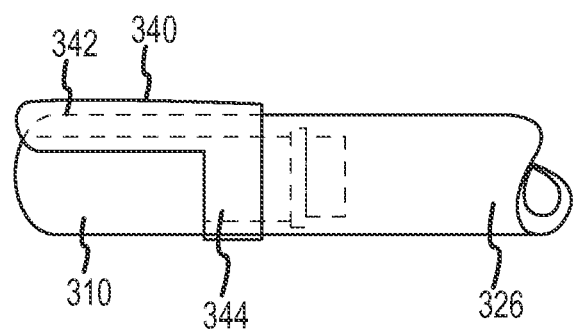
FIG. 53 is a side perspective view of an electrode assembly of the type generally shown in FIG. 52.
Figure 54:
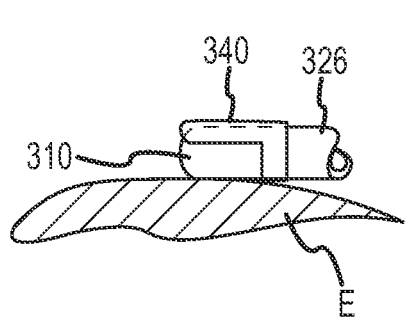
FIG. 54 is a side perspective view of the electrode assembly as generally shown in FIG. 53, the electrode assembly shown in contact with the epicardial surface of the heart.

With some embodiments, the electrode and or electrode assembly may optionally include a means for deflecting or distending adjacent tissue away from a portion of the electrode or the electrode body itself. FIGS. 52-54 disclose embodiments of the present invention wherein a protective member 340 is connected or coupled to either electrode 310 itself or to the distal end of catheter shaft 326. Alternately, protective member 340 may be connected to or coupled with an access sheath or introducer to ensure deflection of adjacent tissue. In an embodiment, protective member 340 may act as a protective shield and provide a helmet-like configuration over the top portion of electrode 310 to deflect tissue from electrode 310. Protective member 340 may be comprised of a thermally and/or electrically nonconductive material such as described above. Protective member 340 may include an extended portion 342 which extends above electrode 310 and reflects the relative shape and size of electrode 310, for example, as shown in FIGS. 52 and 53. Protective member 340 further includes a coupling portion 344 that enables the protective member 340 to be connected and/or coupled to either electrode 310 or catheter shaft 326. The surface of protective member 340, more particularly, the proximal edges of protective member 340 are tapered such that a smooth transition is provided between the catheter shaft and the protective member. Electrode 310 may be a traditional ablation electrode wherein the entire outer surface 314 of electrode 310 is electrically conductive or an alternate configuration of electrode 310 as described in accordance with the embodiments of the present invention may be used.

Figure 55:
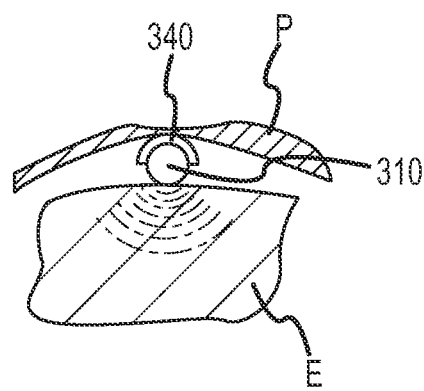
FIG. 55 is a front perspective view of the electrode assembly shown in FIG. 53, the electrode assembly shown positioned in between the epicardial surface of the heart and the pericardial sac.
Figure 56:
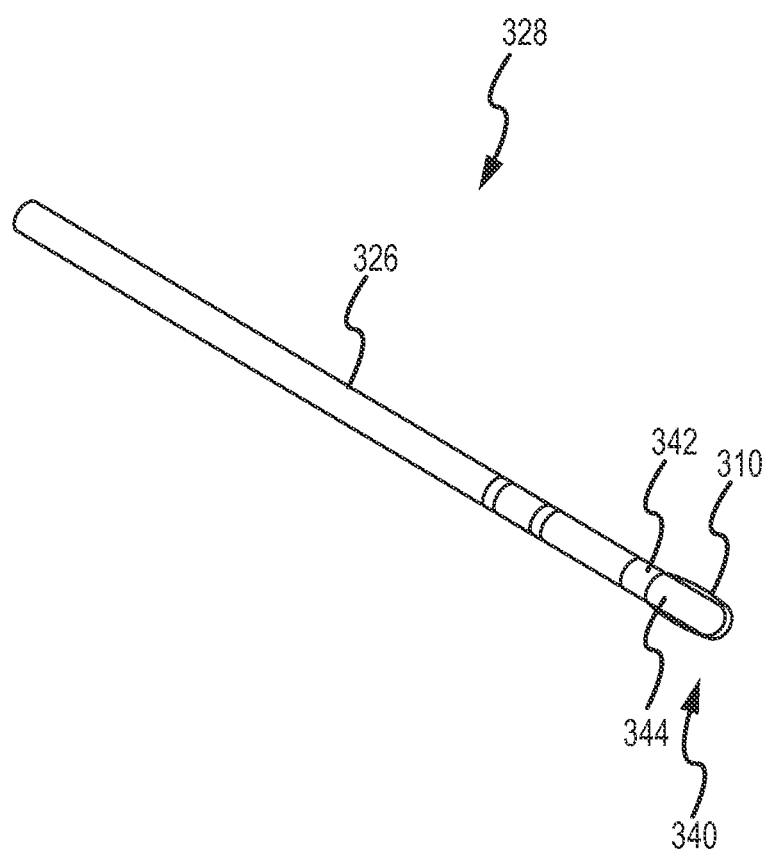
FIG. 56 is a perspective view of a catheter assembly including an electrode assembly of the type generally shown in FIG. 52.

As shown in FIGS. 54 and 55, an electrode 310 with an ablative surface can be placed in contact with target tissue. In particular, protective member 340 may further deflect the pericardial sac, for example, as shown in FIG. 55, thereby ensuring that ablative energy is directed towards the target tissue, i.e. epicardial surface, and the protective member 430 insulates the pericardial surface from receiving unintended ablative energy. FIG. 56 further provides a perspective view of protective member 430 as part of a catheter assembly 328 for use and insertion into an introducer or access sheath. Protective member 340 extends to substantially the length of electrode 310 therein shielding the top portion (not shown) of electrode 310.

Figure 57:
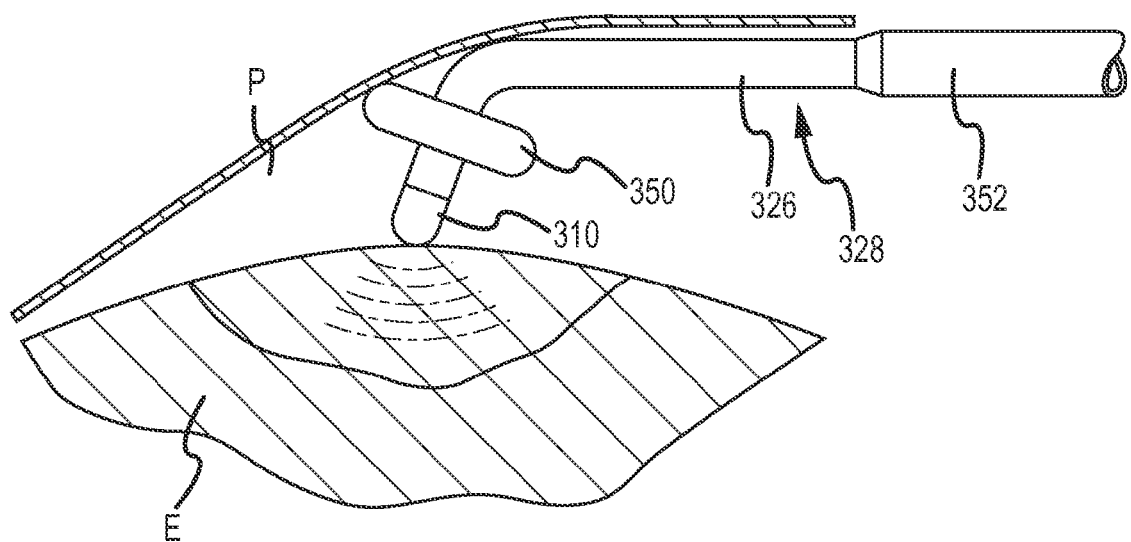
FIG. 57 is an illustrative view of a catheter assembly in accordance with one embodiment of the present invention, the assembly shown inserted within the pericardial sac.

An alternate embodiment of the present invention is shown in FIG. 57, which generally illustrates an alternate means for deflecting or distending adjacent tissue away from a portion of the electrode or the electrode body itself. FIG. 57 illustrates the incorporation of an embodiment of a protective member

350 that is inflatable, such as a balloon or bladder-like embodiment. In accordance with this embodiment, protective member 350 may be filled with a fluid or gas to deflect or distend adjacent tissue away from electrode 310 to ensure that ablative energy is directed only at the target tissue. As illustrated in FIG. 57, the protective member 350 is provided on catheter shaft 26 as part of catheter assembly 328. Upon insertion of catheter assembly 328 into access sheath 352, a protective member 350 may be inflated to deflect the adjacent tissue. The deflection of the adjacent tissue (e.g. pericardial sac, P) helps to better ensure that the ablative energy (e.g. RF energy) is directed principally or even solely, to the target tissue (e.g. the fat pads located on the epicardial surface (E) for the heart when performing ablative therapies for the treatment of atrial fibrillation). Although not shown, protective member 350 may be incorporated directly onto electrode 310 or may be incorporated onto access sheath 352.

The foregoing means for deflecting or distending adjacent tissue or surfaces can among other tings, be configured to further separate ablation portions of the electrode from tissue or areas of the patient that are not intended to be treated; provide additional stability to the electrode relative to the area being treated; and/or provide improved or additional contact force for the ablation portions of the electrode with respect to areas being treated. Moreover, for some embodiment, including those previously described, the means for deflecting or dissenting adjacent tissue may be additionally used to help cool adjacent tissue which may reduce the likelihood of collateral damage to unintended tissue.

As known to those of skill in the art, electrodes and/or electrode tips in accordance with embodiments of the present invention may be configured to be connected to and have their positioning and orientations controlled by pull wires and/or other control means associated with various conventional catheters. The invention contemplates a catheter assembly with such electrodes and/or electrode tips that are shapeable and/or steerable.

Although embodiments of this invention have been described above with a certain degree of particularity, those skilled in the art could make numerous alterations to the disclosed embodiments without departing from the spirit or scope of this invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An electrode tip for an ablation catheter, comprising: an electrode carrier comprising a longitudinal axis, a distally-oriented energy delivery surface and a laterally-oriented energy delivery surface;
   wherein the distally-oriented energy delivery surface consists of a first electrode adapted to direct energy in a forward longitudinal direction;
   wherein the laterally-oriented energy delivery surface comprises a second electrode adapted to direct energy in a first lateral direction and not a second lateral direction, wherein the second electrode is stationary with respect to the electrode carrier, wherein the second electrode is configured to electrically isolate a target tissue and sense electrical signals in the target tissue;
   wherein the second electrode comprises a laterally-facing outer surface electrode that extends along a majority of the longitudinal axis of the electrode carrier, wherein the laterally-facing outer surface electrode comprises an outer surface, wherein the outer surface is bounded by an outer circumference and wherein the outer surface is continuous and uninterrupted within the outer circumference and wherein the first and second electrodes are configured to be selectively, independently activated.

2. The electrode tip of claim 1, wherein at least a portion of the first electrode is insulated or covered with a material to protect non-targeted external tissue or surfaces.

3. The electrode tip of claim 1, wherein at least a portion of the second electrode is insulated or covered with a material to protect non-targeted external tissue or surfaces.

4. The electrode tip of claim 1, wherein the first and second electrodes are configured to be activated simultaneously.

5. The electrode tip of claim 1, wherein the electrode tip includes first and second conductive formations provided along the longitudinal axis that measure a signal transmitted across the electrode tip.

6. The electrode tip of claim 5, wherein the first conduction formation or the second conductive formation comprises the second electrode.

7. The electrode tip of claim 1, including a means for providing cooling to external portions adjacent the first or second electrode.

8. The electrode tip of claim 1, including a closed-loop cooling system for cooling a portion of the tip portion.

9. The electrode tip of claim 1, including a means for deflecting or distending adjacent tissue away from a portion of the electrode tip.

10. The electrode tip of claim 9, wherein the means for deflecting or distending adjacent tissue away from a portion of the electrode tip comprises a protective member connected to the electrode tip, wherein the protective member comprises:
    a first portion configured to have a width greater than a diameter of the electrode tip; and
    a second portion comprising a coupling member configured to connect the first portion to the electrode tip.

11. The electrode tip of claim 9, wherein the means for deflecting or distending adjacent tissue away from a portion of the electrode tip comprises a mechanical distention member configured to be at least partially retracted within the electrode carrier in a first position and configured to be at least partially deployed beyond the electrode carrier in a second position.

12. The electrode tip of claim 11, wherein the mechanical distention member comprises at least one of a wire or plastic extension.

13. The electrode tip of claim 1, wherein the energy directed by at least one of the distally-oriented energy delivery surface and the laterally-oriented energy delivery surface comprises radio frequency, ultrasound, or microwave energy.

14. The electrode tip of claim 1, wherein the second electrode includes an ultrasound transducer that directs ultrasound energy in the lateral direction.

15. The electrode tip of claim 1, wherein the second electrode has a circular arc length that is smaller than a circumference of the electrode tip.

16. The electrode tip of claim 1, wherein a transverse cross-section of the electrode tip is elliptical or oval.

17. The electrode tip of claim 1, wherein the electrode carrier is paddle-shaped.

18. The electrode tip of claim 1, wherein the laterally-oriented energy delivery surface is substantially flat.

19. An electrode tip for an ablation catheter, comprising:
an electrode carrier defining a longitudinal axis and comprising a distally–oriented energy delivery surface and a laterally-oriented energy delivery surface;
wherein the distally-oriented energy delivery surface consists of a first electrode adapted to direct energy in a forward longitudinal direction;
wherein the laterally-oriented energy delivery surface comprises a second electrode, and wherein the second electrode comprises a laterally-facing outer surface electrode extending along a majority of the longitudinal axis of the electrode carrier and adapted to direct energy in a first lateral direction and not a second lateral direction, the laterally-facing outer surface electrode comprising an outer surface, wherein the outer surface is bounded by an outer circumference, wherein the outer surface is continuous and uninterrupted within the outer circumference, and wherein the second electrode is configured to electrically isolate a target tissue and sense electrical signals in the target tissue,
wherein the first and second electrodes are configured to be selectively, independently activated; and wherein the electrode carrier defines a transverse cross-sectional shape when a transverse cross-section is taken across the longitudinal axis of the electrode carrier, the transverse cross-sectional shape comprising a width and a height, wherein the width is greater than the height.

20. The electrode tip of claim 19, wherein the transverse cross-sectional shape of the electrode carrier is elliptical or oval.

21. The electrode tip of claim 19, wherein the transverse cross-sectional shape of the electrode carrier comprises:
a first straight portion;
a second straight portion opposite the first straight portion;
a first curved portion connecting a first end the first straight portion and a first end of the second straight portion; and
a second curved portion connecting a second end of the first straight portion and a second end of the second straight portion.

22. The electrode tip of claim 19, wherein the electrode carrier is paddle-shaped.

23. The electrode tip of claim 19, wherein the laterally-oriented energy delivery surface is substantially flat.

24. The electrode tip of claim 19, wherein the energy directed by at least one of the distally-oriented energy delivery surface and the laterally-oriented energy delivery surface comprises radio frequency, ultrasound, or microwave energy.

25. An ablation catheter comprising:
an electrode tip comprising: an electrode carrier comprising a longitudinal axis, a distally-oriented energy delivery surface and a laterally-oriented energy delivery surface;
wherein the distally-oriented energy delivery surface consists of a first electrode adapted to direct energy in a forward longitudinal direction; wherein the laterally-oriented energy delivery surface comprises a second electrode adapted to direct energy in a first lateral direction and not a second lateral direction, wherein the second electrode is stationary with respect to the electrode carrier, wherein the second electrode is configured to electrically isolate a target tissue and sense electrical signals in the target tissue, wherein the second electrode comprises a laterally-facing outer surface electrode that extends along a majority of the longitudinal axis of the electrode carrier, the laterally-facing outer surface electrode comprising an outer surface, wherein the outer surface is bounded by an outer circumference, and wherein the outer surface is continuous and uninterrupted within the outer circumference; wherein the first and second electrodes are configured to be selectively, independently activated; and
a catheter shaft connected to the electrode tip, the catheter shaft further comprising an orientation marker disposed an outer surface of the catheter shaft substantially opposite the laterally-oriented energy delivery surface, wherein the orientation marker comprises a fluoroscopic material.

* * * * *